US008598316B2

(12) United States Patent
Hanahan et al.

(10) Patent No.: US 8,598,316 B2
(45) Date of Patent: Dec. 3, 2013

(54) MOLECULES THAT SELECTIVELY HOME TO VASCULATURE OF PRE-MALIGNANT DYSPLASTIC LESIONS OR MALIGNANCIES

(75) Inventors: Douglas Hanahan, San Francisco, CA (US); Erkki Ruoslahti, San Francisdo, CA (US)

(73) Assignees: Sanford-Burnham Medical Research Institute, La Jolla, CA (US); The Regents of the University of California, Oakland, CA (US)

( * ) Notice: Subject to any disclaimer, the term of this patent is extended or adjusted under 35 U.S.C. 154(b) by 548 days.

(21) Appl. No.: 12/748,249

(22) Filed: Mar. 26, 2010

(65) Prior Publication Data

US 2011/0002848 A1    Jan. 6, 2011

Related U.S. Application Data

(63) Continuation of application No. 10/970,847, filed on Oct. 20, 2004, now Pat. No. 7,723,474.

(60) Provisional application No. 60/513,407, filed on Oct. 21, 2003.

(51) Int. Cl.
*A61K 38/08* (2006.01)
*A61K 38/00* (2006.01)

(52) U.S. Cl.
USPC ........................... 530/329; 530/317; 514/13.3

(58) Field of Classification Search
None
See application file for complete search history.

(56) References Cited

U.S. PATENT DOCUMENTS

| | | | |
|---|---|---|---|
| 3,929,758 A * | 12/1975 | Hughes et al. | ................ 530/307 |
| 5,318,899 A | 6/1994 | Scarborough et al. | |
| 5,622,699 A | 4/1997 | Ruoslahti et al. | |
| 5,789,542 A | 8/1998 | McLaughlin et al. | |
| 6,068,829 A | 5/2000 | Ruoslahti et al. | |
| 6,232,287 B1 | 5/2001 | Ruoslahti et al. | |
| 6,296,832 B1 | 10/2001 | Ruoslahti et al. | |
| 6,306,365 B1 | 10/2001 | Ruoslahti et al. | |
| 6,528,481 B1 * | 3/2003 | Burg et al. | .................... 424/93.6 |
| 6,610,651 B1 | 8/2003 | Ruoslahti et al. | |
| 6,933,281 B2 | 8/2005 | Ruoslahti et al. | |
| 7,018,615 B2 | 3/2006 | Ruoslahti et al. | |
| 2002/0045737 A1 | 4/2002 | Choi et al. | |

FOREIGN PATENT DOCUMENTS

| | | | |
|---|---|---|---|
| WO | WO 99/46284 | 9/1999 | |
| WO | WO 00/48464 | 8/2000 | |
| WO | WO 01/81581 A2 * | 11/2001 | ............. C12N 15/31 |

OTHER PUBLICATIONS

Alvarez-Bravo et al., "Novel synthetic antimicrobial peptides effective against methicillin-resistant *Staphylococcus aureus*," *Biochem. J.* 302:535-538 (1994).

Arap et al., "Cancer Treatment by Targeted Drug Delivery to Tumor Vasculature in a Mouse Model," *Science* 279:377-380 (1998).
Arbeit et al., "Progressive Squamous Epithelial Neoplasia in K14-Human Papillomavirus Type 16 Transgenic Mice," *J. Virol.* 68:4358-4368 (1994).
Arbeit et al., "Upregulation of Fibroblast Growth Factors and Their Receptors During Multi-Stage Epidermal Carcinogenesis in K14-HPV16 Transgenic Mice," *Oncogene* 13:1847-1857 (1996).
Bergers et al., "Benefits of Targeting Both Pericytes and Endothelial Cells in the Tumor Vasculature With Kinase Inhibitors," *J. Clin. Invest.* 111:1287-1295 (2003).
Bergers et al., "Effects of Angiogenesis Inhibitors on Multistage Carcinogenesis in Mice," *Science* 284:808-812 (1999).
Bessalle et al., "All-D-magainin: chirality, antimicrobial activity and proteolytic resistance," *FEBS Lett.* 274:151-155 (1990).
Blondelle and Houghten, "*Annual Reports in Medicinal Chemistry*," pp. 159-168, Academic Press (1992).
Blondelle and Houghten, "Design of model amphipathic peptides having potent antimicrobial activities," *Biochem.* 31:12688-12694 (1992).
Boehme et al., "Antiangiogenic Therapy of Experimental Cancer Does Not Induce Acquired Drug Resistance," *Nature* 390:404-407 (1997).
Bregman and Meyskens, "Difluoromethylornithine Enhances Inhibition of Melanoma Cell Growth in Soft Agar by Dexamethasone, Clone A Interferon and Retinoic Acid," *Int. J. Cancer* 37:101-107 (1986).
Burg et al., "$NG_2$ Proteoglycan-Binding Peptides Target Tumor Neovasculature," *Cancer Res.* 59:2869-2874 (1999).
Carmeliet and Jain, "Angiogenesis in Cancer and Other Diseases," *Nature* 407:249-257 (2000).
Castronovo and Belotti, "TNP-470 (AGM-1470): Mechanisms of Action and Early Clinical Development," *Eur. J. Cancer* 32A: 2520-2527 (1996).
Chan et al., "Prospective Randomized Trial of Docetaxel Versus Doxorubicin in Patients With Metastatic Breast Cancer," *J. Clin. Oncol.* 17:2341-2354 (1999).
Chang et al., "Mosaic Blood Vessels in Tumors: Frequency of Cancer Cells in Contact With Flowing Blood," *Proc. Natl. Acad. Sci. U.S.A.* 97:14608-14613 (2000).
Chaudhry et al., Expression of Platelet-Derived Growth Factor and Its Receptors in Neuroendocrine Tumors of the Digestive System, *Canc. Res.* 52:1006-1012.
Chavatte et al., "Rhenium (Re) and Technetium (Tc)-99M Oxocomplexes of Neurotensin(8-13)," *J. Labelled Cpd. Radiopharm.* 42:415-421 (1999).

(Continued)

*Primary Examiner* — Cecilia J Tsang
*Assistant Examiner* — Li Lee
(74) *Attorney, Agent, or Firm* — Jenkins, Wilson, Taylor & Hunt, P.A.

(57) ABSTRACT

The present invention provides a conjugate that contains a therapeutic moiety linked to a homing peptide or peptidomimetic which selectively homes to vasculature of pre-malignant dysplastic skin and which includes the amino acid sequence SRPRR (SEQ ID NO: 1) or a conservative variant or peptidomimetic thereof. The present invention further provides a conjugate containing a therapeutic moiety linked to a homing peptide or peptidomimetic which selectively homes to vasculature of malignant skin and which includes the amino acid sequence CGKRK (SEQ ID NO: 6) or the amino acid sequence CDTRL (SEQ ID NO: 7), or a conservative variant or peptidomimetic of one of these sequences.

43 Claims, 4 Drawing Sheets

(56) References Cited

OTHER PUBLICATIONS

Coussens et al., "Genetic Predisposition and Parameters of Malignant Progression in K14-HPV16 Transgenic Mice," *Amer. J. Pathol.* 149:1899-1917 (1996).
Craggs and Kellie, "A Functional Nuclear Localization Sequence in the C-Terminal Domain of SHP-1," *J. Biol. Chem.* 276:23719-23725 (2001).
Crown, "The Platinum Agents: A Role in Breast Cancer Treatment?" *Seminars in Oncol.* 28:28-37 (2001).
Diamandis et al., "The New Human Kallikrein Gene Family: Implications in Carcinogenesis," *Trends Endocrinol Metab.* 11:54-60 (2000).
El-Sheikh et al., "A Novel Vascular Endothelial Growth Factor Heparin-Binding Domain Substructure Binds to Glycosaminoglycans In Vivo and Localizes to Tumor Microvascular Endothelium," *Cancer Res.* 62:7118-7123 (2002).
Fadok et al., "A Receptor for Phosphatidylserine-Specific Clearance of Apoptotic Cells," *Nature* 405:85-90 (2000).
Gomis-Ruth, "The Structure of Human Prokallikrein 6 Reveals a Novel Activation Mechanism for the Kallkrein Family," *J. Biol. Chem.* 277:27273-27281 (2002).
Griffith et al., "Methionine Aminopeptidase (Type 2) is the Common Target for Angiogenesis Inhibitors AGM-1470 and Ovalicin," *Chem. Biol.* 4:461-471 (1997).
Guy et al., "Induction of Mammary Tumors by Expression of Polyomavirus Middle T Oncogene: A Transgenic Mouse Model for Metastatic Disease," *Moll.Cell.Biol.* 12:954-961 (1992).
Hagedorn and Bikfalvi, "Target Molecules for Anti-Angiogenic Therapy: From Basic Research to Clinical Trials," *Crit. Rev. Oncol. Hematol.* 34:89-110 (2000).
Hanahan and Weinberg, "The Hallmarks of Cancer," *Cell* 100:57-70 (2000).
Hanahan, D., "Heritable Formation of Pancreatic Beta-Cell Tumours in Transgenic Mice Expressing Recombinant Insulin/Simian Virus 40 Oncogenes," *Nature* 315:115-122 (1985).
Heidtmann et al., "Generation of Angiostatin-Like Fragments From Plasminogen by Prostate-Specific Antigen," *Br. J. Cancer* 81:1269-1273 (1999).
Hoffman, "Progressive Vascular Change in a Transgenic Mouse Model of Squamous Cell Carcinoma," *Cancer Cell* 4:383-391 (2003).
Homandberg et al., "Heparin-binding Fragments of Fibronectin Are Potent Inhibitors of Endothelial Cell Growth," *Am. J. Path.* 120:327-332 (1985).
Homandberg et al., "Heparin-binding Fragments of Fibronectin are Potent Inhibitors of Endothelial Cell Growth: Structure-Function Correlations," *Biochim. Biophys. Acta* 874:61-71 (1986).
Hurley, L.H., "DNA and Its Associated Processes as Targets for Cancer Therapy," *Nat. Rev. Cancer* 2:188-200 (2002).
Ingber et al., "Synthetic Analogues of Fumagillin That Inhibit Angiogenesis and Suppress Tumour Growth," *Nature* 348:555-557 (1990).
Javadpour et al., "De novo antimicrobial peptides with low mammalian cell toxicity," *J. Med. Chem.* 39:3107-3113 (1996).
Jia et al., "Peptides Encoded by Exon 6 of VEGF Inhibit Endothelial Cell Biological Responses and Angiogenesis Induced by VEGF," *Biochem. Biophys. Res. Commun.* 283:164-173 (2001).
Jonca et al., "Cell Release of Bioactive Fibroblast Growth Factor 2 by Exon 6-Encoded Sequence of Vascular Endothelial Growth Factor," *J. Biol. Chem.* 272:24203-24209 (1997).
Joyce et al., "Stage Specific Vascular Markers Revealed by Phage Display in a Mouse Model of Pancreatic Islet Tumorigenesis," *Cancer Cell.* 4:393-403 (2003).
Kawai et al, "Functional Annotation of a Full-Length Mouse cDNA Collection," *Nature* 409:685-690 (2001).
Kirsch et al., "Anti-angiogenic Treatment Strategies for Malignant Brain Tumors," *J. Neurooncol.* 50:149-163 (2000).
Laakkonen et al., "A Tumor-homing Peptide With a Targeting Specificity Related to Lymphatic Vessels," *Nat. Med.* 8:751-755 (2002).
LeCouter et al., "The Endocrine-gland-derived VEGF Homologue Bv8 Promotes Angiogenesis in the Testis: Localization of Bv8 Receptors to Endothelial Cells," *Proc. Natl. Acad. Sci. U.S.A.* 100:2685-2690 (2003).
Majoul et al., "Reduction of protein disulfide bonds in an oxidizing environment. The disulfide bridge of cholera toxin A-subunit is reduced in the endoplasmic reticulum," *FEBS Lett.* 401(2-3):104-108 (1997).
Maloy and Kari, "Structure-activity studies on magainins and other host defense peptides," *Biopolymers* 37:105-122 (1995).
Mancheno et al., "A peptide of nine amino acid residues from alpha-sarcin cytotoxin is a membrane-perturbing structure," *J. Peptide Res.* 51:142-148 (1998).
Miao et al, "Kallistatin is a New Inhibitor of Angiogenesis and Tumor Growth," *Blood* 100:3245-3252 (2002).
O'Reilly et al., "Angiostatin induces and sustains dormancy of human primary tumors in mice," *Nature Med.* 2:689-692 (1996).
O'Reilly et al., "Angiostatin: A Novel Angiogenesis Inhibitor That Mediates the Suppression of Metastases by a Lewis Lung Carcinoma," *Cell* 79:315-328 (1994).
O'Reilly et al., "Antiangiogenic Activity of the Cleaved Conformation of the Serpin Antithrombin," *Science* 285:1926-1928 (1999).
O'Reilly et al., "Endostatin: An Endogenous Inhibitor of Angiogenesis and Tumor Growth," *Cell* 88:277-285 (1997).
Paridaens et al., "Paclitaxel Versus Doxorubicin as First-Line Single-Agent Chemotherapy for Metastatic Breast Cancer: A European Organization for Research and Treatment of Cancer Randomized Study With Cross-over," *J. Clin. Oncol.* 18:724-733 (2000).
Pasqualini et al, "Probing the Structural and Molecular Diversity of Tumor Vasculature," *Trends Mol. Med.* 8:563-571 (2002).
Porkka et al, "A Fragment of the HMGN2 Protein Homes to the Nuclei of Tumor Cells and Tumor Endothelial Cells In Vivo," *Proc. Natl. Acad. Sci. U.S.A.* 99:7444-7449 (2002).
Price et al., "Tumorigenicity and Metastasis of Human Breast Carcinoma Cell Lines in Nude Mice," *Cancer Res.* 50:717-721 (1990).
Ran et al, "Increased Exposure of Anionic Phospholipids on the Surface of Tumor Blood Vessels," *Cancer Res.* 62:6132-6140 (2002).
Reitermann et al., "Lipopeptide derivatives of bacterial lipoprotein constitute potent immune adjuvants combined with or covalently coupled to antigen or hapten," *Biol. Chem. Hoppe Seyler.* 370(4):343-352 (1989).
Roghani and Moscatelli, "Basic Fibroblast Growth Factor Is Internalized Through Both Receptor-Mediated and Heparin Sulfate-Mediated Mechanisms," *J. Biol. Chem* 267:22156-22162 (1992).
Rudinger, J., In: Peptide Hormomes, JA Parsons, Ed. pp. 1-7 (1976).
Ruoslahti, E., "Specialization of Tumour Vasculature," *Nat. Rev. Cancer* 2:83-90 (2002).
Sin et al. "The Anti-Angiogenic Agent Fumagillin Covalently Binds and Inhibits the Methionine Aminopeptidase, MetAP-2,"*Proc. Natl. Acad. Sci. U.S.A.* 94:6099-6103 (1997).
Smilek et al., "A single amino acid change in a myelin basic protein peptide confers the capacity to prevent rather than induce experimental autoimmune encephalomyelitis," *Proc. Natl. Acad. Sci. U. S. A.* 88(21):9633-9637 (1991).
Talbot and Brown, "Experimental and Clinical Studies on the Use of Matrix Metalloproteinase Inhibitors for the Treatment of Cancer," *Eur. J. Cancer* 32A:2528-2533 (1996).
Thurston et al, "Cationic Liposomes Target Angiogenic Endothelial Cells in Tumors and Chronic Inflammation in Mice," *J. Clin. Invest.* 101:1401-1413 (1998).
Voet, D. and Voet, J.G, Biochemistry, 2nd Edition, pp. 179 and 235-241 (1995).
W.S. Messer, "Vasopressin and Oxytocin," web document updated Apr. 3, 2000; Five pages from URL: http://www.neurosci.pharm.utoledo.edu/MBC3320/vasopressin.htm.
Yousef and Diamandis, "The Expanded Human Kallikrein Gene Family: Locus Characterization and Molecular Cloning of a New Member, KLK-L3 (KLK9)," *Genomics* 65:184-194 (2000).
Yousef et al, "Quantitative Expression of the Human Kallikrein Gene 9 (*KLK9*) in Ovarian Cancer: A New Independent and Favorable Prognostic Marker," *Cancer Res.* 61:7811-7818 (2001).
Yousef et al., "Identification of Novel Human Kallikrein-Like Genes on Chromosome 19q13-q13.4," *Anticancer Res.* 19:2843-2852 (1999).
Zhou et al, "Identification of the Nuclear Localization Signal of Human Papillomavirus Type 16 L1 Protein," *Virology* 185:625-632 (1991).

\* cited by examiner

US 8,598,316 B2

MOLECULES THAT SELECTIVELY HOME TO VASCULATURE OF PRE-MALIGNANT DYSPLASTIC LESIONS OR MALIGNANCIES

This invention was made with government support under CA 82713, CA 30199, and CA 37395 awarded by the National Cancer Institute. The government has certain rights in this invention.

This application is a continuation of U.S. Ser. No. 10/970,847, filed Oct. 20, 2004, now U.S. Pat. No. 7,723,474, which claims benefit of provisional application Ser. No. 60/513,407, filed Oct. 21, 2003, which are herein incorporated by reference.

BACKGROUND OF THE INVENTION

1. Field of the Invention

The present invention relates generally to the fields of cancer and cancer progression, molecular medicine and drug delivery and, more specifically, to molecules that selectively home to vasculature of pre-malignant dysplastic lesions or to vasculature of malignancies.

2. Background Information

A major hurdle to advances in preventing or treating cancer is the lack of agents that are effective in selectively targeting a cancer or pre-cancerous tissue while sparing normal cells. Radiation therapy and surgery, for example, which generally are localized treatments, can cause substantial damage to normal tissue in the treatment field, resulting in scarring and loss of normal tissue. Furthermore, chemotherapy, which generally is administered systemically, can cause substantial damage to normal organs such as normal skin, bone marrow, mucosa, and small intestine, which undergo rapid cell turnover and continuous cell division. As a result, undesirable side effects such as nausea, loss of hair and drop in blood cell count occur as a result of systemic treatment with a chemotherapeutic agent. Such undesirable side effects often limit the amount of drug that can be safely administered, thereby reducing survival rate and impacting the quality of patient life.

Selective delivery of therapeutics such as anti-angiogenic agents to vasculature that supports tumors would result in less toxic therapy since rapidly proliferating normal cells would be spared. Similarly, selective delivery of anti-angiogenic agents to vasculature of dysplastic cells that are not yet malignant would provide a prophylactic strategy for reducing the risk of cancer. However, to date, it has been difficult to produce drugs that are delivered specifically to tumor vasculature or the vasculature of dysplastic, pre-malignant tissues. Thus, there is a need for molecules that selectively target malignant tissue such as malignant skin, as well as for molecules that selectively target pre-malignant dysplastic tissues such as pre-malignant dysplastic skin. The present invention satisfies these needs and also provides related advantages.

SUMMARY OF THE INVENTION

The present invention provides a conjugate that contains a therapeutic moiety linked to a homing peptide or peptidomimetic which selectively homes to vasculature of pre-malignant dysplastic skin and which includes the amino acid sequence SRPRR (SEQ ID NO: 1) or a conservative variant or peptidomimetic thereof.

The present invention also provides a method of directing a moiety to vasculature of a pre-malignant dysplastic tissue in a subject by administering to the subject a conjugate containing a moiety linked to a homing molecule which selectively homes to vasculature of pre-malignant dysplastic skin and which specifically binds a cognate receptor for CSRPRRSEC (SEQ ID NO: 3), thereby directing the moiety to vasculature of the pre-malignant dysplastic tissue.

Further provided herein is a method of imaging vasculature of a pre-malignant dysplastic tissue by administering to the subject a conjugate containing a detectable moiety linked to a homing molecule which selectively homes to vasculature of pre-malignant dysplastic skin and which specifically binds a cognate receptor for CSRPRRSEC (SEQ ID NO: 3); and detecting the conjugate, thereby imaging vasculature of the pre-malignant dysplastic tissue.

The present invention also provides a method of reducing the risk of progression to a malignancy in a subject by administering to the subject a conjugate containing a therapeutic moiety linked to a homing molecule which selectively homes to vasculature of pre-malignant dysplastic skin and which specifically binds a cognate receptor for CSRPRRSEC (SEQ ID NO: 3), thereby diminishing vasculature of a pre-malignant dysplastic tissue and reducing the risk of progression to the malignancy.

Also provided herein is a conjugate containing a therapeutic moiety linked to a homing peptide or peptidomimetic which selectively homes to vasculature of malignant skin and which includes the amino acid sequence CGKRK (SEQ ID NO: 6) or the amino acid sequence CDTRL (SEQ ID NO: 7), or a conservative variant or peptidomimetic of one of these sequences.

The present invention further provides a method of directing a moiety to vasculature of a malignant tissue in a subject by administering to the subject a conjugate containing a moiety linked to a homing molecule which selectively homes to vasculature of malignant skin and which specifically binds a cognate receptor for SEQ ID NO: 6 or SEQ ID NO: 7, thereby directing the moiety to vasculature of the malignant tissue.

Additionally provided by the present invention is a method of imaging vasculature of a malignant tissue by administering to the subject a conjugate containing a detectable moiety linked to a homing molecule which selectively homes to vasculature of malignant skin and which specifically binds a cognate receptor for SEQ ID NO: 6 or SEQ ID NO: 7; and detecting the conjugate, thereby imaging vasculature of the malignant tissue.

The present invention also provides a method of treating a cancer in a subject by administering to the subject a conjugate containing a therapeutic moiety linked to a homing molecule which selectively homes to vasculature of malignant skin and which specifically binds a cognate receptor for SEQ ID NO: 6 or SEQ ID NO: 7, thereby directing the therapeutic moiety to vasculature of the cancer and treating the cancer.

Further provided by the present invention is a method of staging tumor progression in a subject having or suspected of having a pre-malignant lesion or tumor by administering to the subject a conjugate containing a detectable moiety linked to (i) a homing molecule which selectively homes to vasculature of pre-malignant dysplastic skin and which specifically binds a cognate receptor for CSRPRRSEC (SEQ ID NO: 3), or (ii) a homing molecule which selectively homes to vasculature of malignant skin and which specifically binds a cognate receptor for SEQ ID NO: 6 or SEQ ID NO: 7; and detecting the conjugate, where detection of the conjugate containing a homing molecule which selectively homes to vasculature of pre-malignant dysplastic skin indicates a pre-malignant stage of tumor progression in the subject and where detection of the conjugate containing a homing molecule which selectively homes to vasculature of malignant skin indicates a malignant stage of tumor progression in the subject.

The present invention further provides an isolated peptide or peptidomimetic which has a length of less than 20 residues and includes the amino acid sequence SRPRR (SEQ ID NO: 1) or a peptidomimetic thereof. Also provided herein is an isolated peptide or peptidomimetic which has a length of less than 90 residues and which includes the amino acid sequence CXSRPRRZC (SEQ ID NO: 2) or a peptidomimetic thereof, where X=0 to 20 independently selected residues and Z=0 to 20 independently selected residues.

In addition, there is provided by the present invention an isolated peptide or peptidomimetic which has a length of less than 20 residues and which includes the amino acid sequence CGKRK (SEQ ID NO: 6) or a peptidomimetic thereof. Further provided herein is an isolated peptide or peptidomimetic which has a length of less than 20 residues and which includes the amino acid sequence CDTRL (SEQ ID NO: 7) or a peptidomimetic thereof.

DETAILED DESCRIPTION OF THE INVENTION

Figure 1:
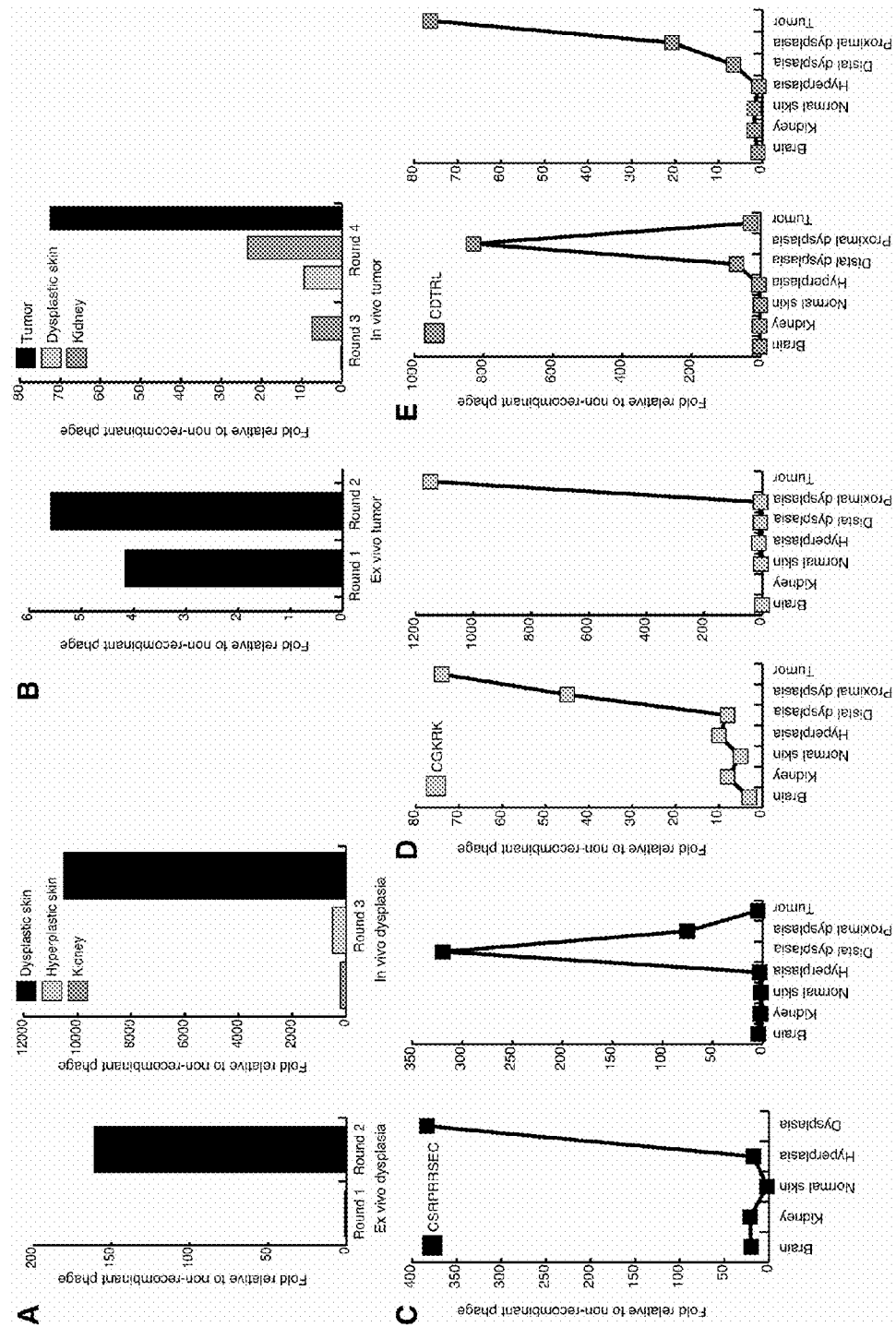
FIG. 1 shows that phage-displayed peptides selectively home to dysplastic skin lesions and tumors. Ex vivo and in vivo selections of phage were performed for binding and homing to (A) dysplastic skin lesions or (B) skin tumors. (C) In vivo homing of CSRPRRSEC (SEQ ID NO: 3) phage from the dysplastic skin screen to dysplastic skin lesions of a 4 to 6 month-old K14HPV16 mouse (left) and to dysplastic skin lesions and tumor of a 9 to 12 month-old K14HPV16 mouse (right). In vivo homing of (D) CGKRK (SEQ ID NO: 6) and (E) CDTRL (SEQ ID NO: 7) peptides from tumor screening to tumors and other tissues in K14HPV16 mice. Results from two different tumor-bearing mice are shown for each peptide. Normal skin values shown in panels C to E are from parallel experiments in wild-type FVB/n mice.

The present invention is directed to molecules that selectively home to vasculature of pre-malignant dysplastic skin and further directed to molecules that selectively home to vasculature of malignant skin. As disclosed herein in Example I, peptides specific for pre-malignant, dysplastic lesions were isolated using a combination of in vivo and ex vivo selections on 4 to 6 month old K14-HPV16 mice with dysplastic skin lesions but no macroscopic evidence of tumors. Sequential ex vivo selections using suspensions of dysplastic skin cells resulted in a 160-fold enrichment of phage relative to enrichment of non-recombinant phage lacking displayed peptides (FIG. 1A, left); greater than 10,000-fold enrichment resulted from the subsequent round of in vivo selection (FIG. 1A, right).

To test homing specificity of selected peptides, purified phage displaying a single recombinant sequence were intravenously injected into K14HPV16 mice bearing protuberant ear or trunk tumors at 9 to 12 months of age to assess homing to squamous cell carcinomas, or alternatively injected into younger K14HPV16 mice presenting with multifocal dysplasias but no tumors. Both neoplastic tissues and normal control organs were collected and assayed for phage accumulation.

Peptides displayed on several of the selected phage clones were found to be highly selective for dysplastic skin, and did not appreciably home to normal organs. One of these dysplasia-homing peptides, CSRPRRSEC (SEQ ID NO: 3), appeared three times amongst the 48 phage sequenced from the in vivo round, along with two variants, CSRPRRSVC (SEQ ID NO: 4) and CSRPRRSWC (SEQ ID NO: 5), that each appeared once. As disclosed herein in FIG. 1C, left panel, phage displaying peptide CSRPRRSEC (SEQ ID NO: 3) were enriched ~350-fold in dysplastic skin and did not significantly accumulate in control tissues. Furthermore, when injected into a K14HPV16 mouse bearing an ear tumor and multifocal skin dysplasias, CSRPRRSEC (SEQ ID NO: 3)-displaying phage effectively homed to dysplastic chest skin and dysplastic ear skin with little homing to the tumor (see FIG. 1C, right panel). In addition, CSRPRRSEC (SEQ ID NO: 3)-bearing phage did not home to normal skin of FVB/n mice in vivo and further did not bind to hyperplastic skin of 1 to 2 month-old K14-HPV16 mice in ex vivo experiments (FIG. 1C, left and right panels). Results disclosed herein further indicate that the dysplasia-homing sequence, CSRPRRSEC (SEQ ID NO: 3), is homologous to the $C_{220}SRPRR_{225}$ (SEQ ID NO: 17) loop that defines substrate specificity in human kallikrein 9 (human KLK-9), a protease of the trypsin super-family which is a positive prognostic marker in breast and ovarian cancer. Thus, a peptide mimicking the active site loop of human kallikrein 9 binds to blood vessels of pre-malignant or angiogenic dysplasias but not to blood vessels associated with a malignancy.

These results demonstrate that peptide CSRPRRSEC (SEQ ID NO: 3) selectively homes to dysplastic skin lesions and further indicate that this peptide binds to a receptor which is present in skin dysplasias but which is essentially absent or inaccessible via the circulation in normal skin and in squamous cell carcinomas. In view of the localization of this peptide to endothelial cells, these results further indicate that homing selectivity of peptide SEQ ID NO: 3 is attributable to vascular changes during the carcinogenic progression from normal skin to dysplasia and from dysplasia to cancer.

As further disclosed herein in Example II, phage that selectively home to squamous cell carcinomas (SCCs) were isolated by two rounds of ex vivo panning followed by two rounds of in vivo panning in K14-HPV16 mice having tumors histologically confirmed as squamous cell carcinoma grades II-IV (Coussens et al., *Am. J. Pathol.* 149:1899-1917 (1996)). As shown in FIG. 1B, phage enrichment relative to non-recombinant phage rose from 6-fold in the second ex vivo round to greater than 70-fold relative to non-recombinant phage in the second in vivo round, which was the fourth sequential round overall. After sequencing of almost 200 phage clones, several were chosen for further analysis based on their frequency and increased prevalence in in vivo selections. Of the fifteen chosen clones, phage displaying CGKRK (SEQ ID NO: 6), CGTKRKC (SEQ ID NO: 11), CDTAVVEGL (SEQ ID NO: 12) or CDTRL (SEQ ID NO: 7) bound to a K14-HPV16 tumor-derived cell suspension ex vivo.

Furthermore, upon intravenous injection into tumor-bearing K14-HPV16 mice, CGKRK (SEQ ID NO: 6) phage showed a marked preference for tumors. Similar analysis of the CDTRL (SEQ ID NO: 7) phage revealed a variable preference for squamous cell carcinomas and dysplastic lesions; in one experiment the phage accumulated more effectively in dysplastic lesions than in a tumor, whereas the reverse was true in another experiment, indicative of lesional heterogeneity in the CDTRL (SEQ ID NO: 7) cognate receptor (FIG. 1E). In both cases, phage showed little affinity for normal or hyperplastic skin (FIG. 1E).

Figure 2:
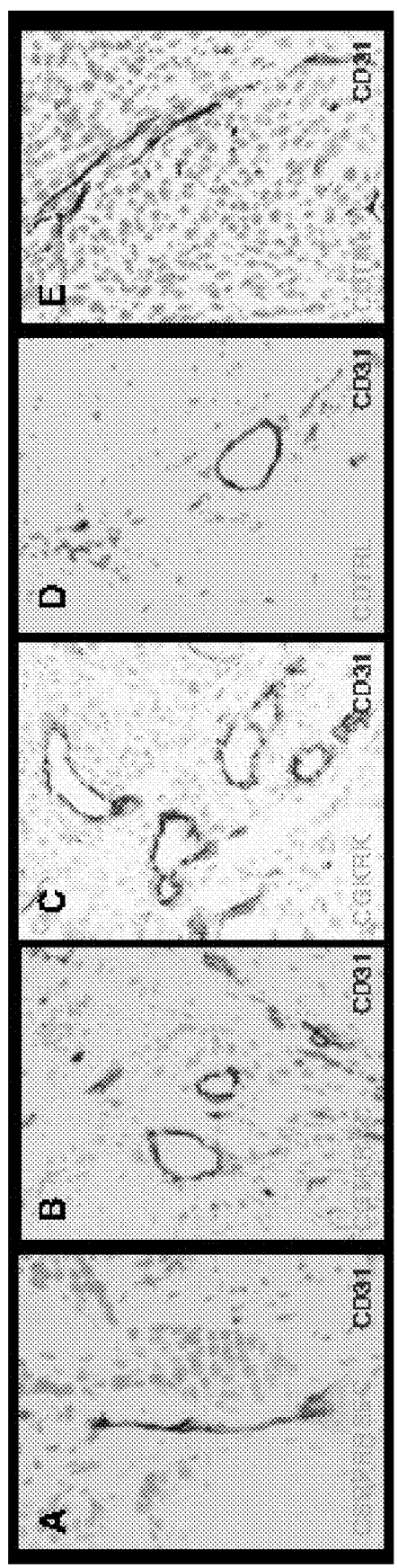
FIG. 2 shows vascular localization of homing phage. K14HPV16 mice with dysplastic skin lesions or tumors were intravenously injected with individual homing phage before sacrificing mice 10 minutes later, and detecting phage in tissue sections with rabbit anti-T7 phage antisera (Alexa594). Blood vessels were stained with rat anti-mouse CD31 (Alexa488). (A) CSRPRRSEC (SEQ ID NO: 3)-displaying phage co-localize with CD31 in the dysplastic skin lesions of 4-6 month-old dysplastic mice. (B and C) Tumor-homing CGKRK (SEQ ID NO: 6)-phage home to CD31-positive vessels in dysplasias and skin tumors. (D and E) Tumor-homing CDTRL (SEQ ID NO: 7)-phage phage home to CD31-positive vessels in dysplasias and skin tumors. Magnifications shown are 200×.

To further characterize homing selectivity, dysplasia-homing phage bearing CSRPRRSEC (SEQ ID NO: 3) were intravenously injected into 4 to 6 month-old dysplasia-bearing mice. In parallel, 9 to 12 month-old tumor-bearing mice were infused with the tumor-homing phage CGTKRKC (SEQ ID NO: 11), CGKRK (SEQ ID NO: 6) or CDTRL (SEQ ID NO: 7). As shown in FIG. 2, phage co-localized in each case with CD31-positive endothelial cells in the expected target tissue. In particular, CSRPRRSEC (SEQ ID NO: 3)-phage accumulated in dysplastic skin (FIG. 2A) of mice bearing dysplasias but no tumors, and CGTKRKC (SEQ ID NO: 11) phage were detected to a lesser extent in dysplastic skin of tumor-bearing mice (FIG. 2B). In addition, CGKRK (SEQ ID NO: 6) phage accumulated in tumor tissue (FIG. 2C), and CDTRL (SEQ ID NO: 7) phage were localized to large, dilated vessels throughout dysplastic and hyperplastic skin (FIG. 2D) as well as in tumors (FIG. 2E).

Figure 3:
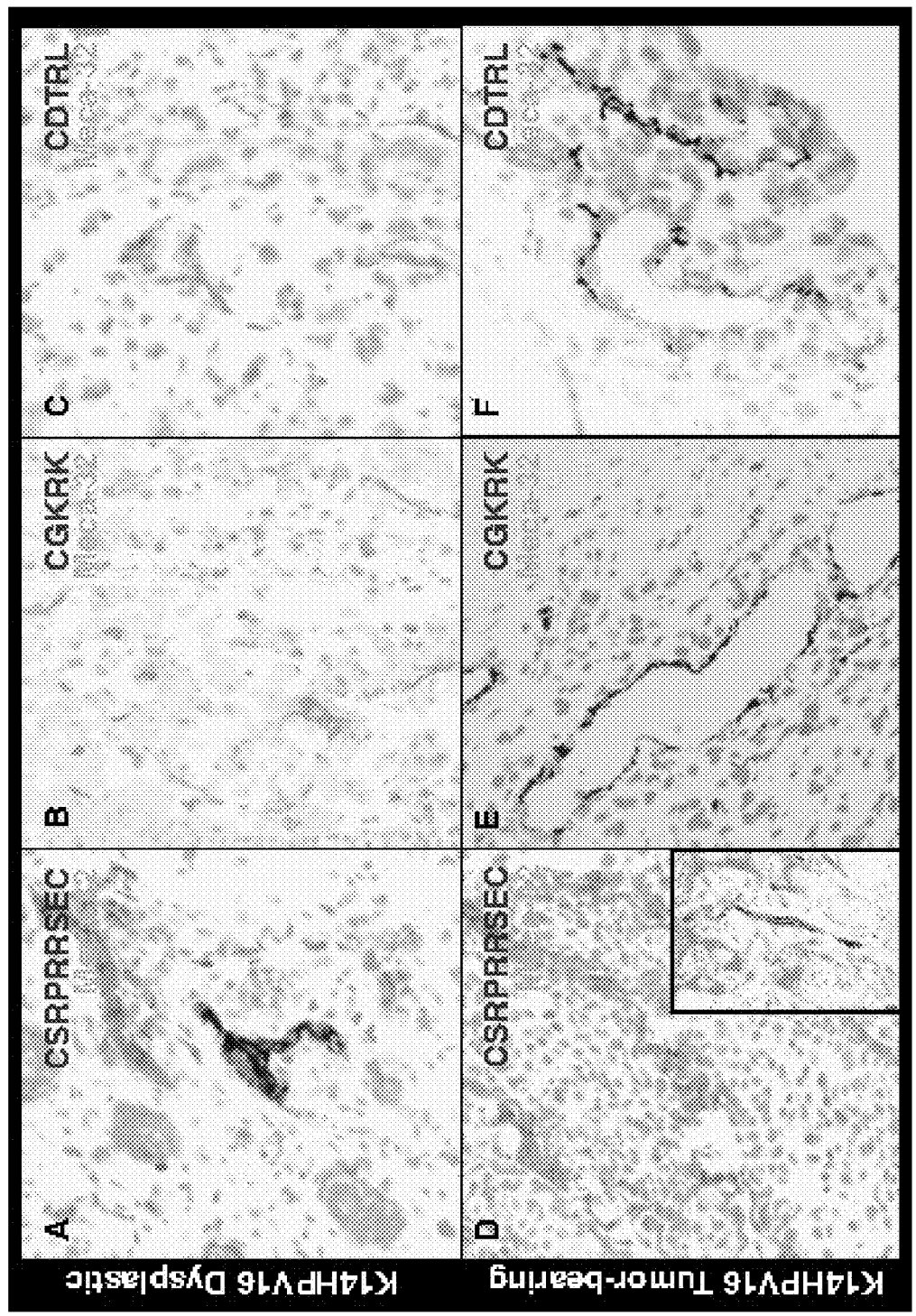
FIG. 3 shows that fluorescein-labeled peptides co-localize with a vascular marker. Fluorescein-labeled peptides were intravenously injected into mice with dysplastic skin lesions or tumors before sacrificing mice 10 minutes later and analyzing peptide localization in tissues sections. Fluorescein-CSRPRRSEC (SEQ ID NO: 3) co-localizes with Meca-32 in the vasculature of dysplastic skin (A) but not in tumor tissue (D). The CSRPRRSEC (SEQ ID NO: 3) peptide continues to recognize the vasculature of dysplastic skin in tumor-bearing mice (D inset) but does not recognize pre-malignant lesions (angiogenic islets) in RIP1-Tag2 mice. Fluorescein-labeled CGKRK (SEQ ID NO: 6) and CDTRL (SEQ ID NO: 7) peptides were not detected in dysplastic skin from 4-6 month-old mice (B and C), but co-localized with Meca-32 in tumor vasculature (E and F). Magnifications shown are 200×.

Synthetic peptides having homing sequences were also analyzed outside of the context of phage particles. Both younger dysplasia-bearing and older tumor-bearing K14-HPV16 mice were injected with fluorescein-labeled peptides. As shown in FIG. 3, fluorescein-labeled peptides co-localized with the cell-surface endothelial marker Meca-32 in target neoplastic tissue after intravenous injection, and were not detected in tissues where the corresponding phage did not home. Specifically, fluorescein-labeled CSRPRRSEC (SEQ ID NO: 3) co-localized with Meca-32 in dysplastic skin vasculature from both non-tumor-bearing (FIG. 3A) and tumor-bearing mice (FIG. 3D, inset). As is evident in FIG. 3D, peptide SEQ ID NO: 3 was not detected within squamous tumors, confirming the selectivity of this peptide for pre-malignant dysplastic vasculature. In contrast, fluorescein-labeled CGKRK (SEQ ID NO: 6) and CDTRL (SEQ ID NO: 7) peptides were not detected in the dysplastic skin of younger non-tumor bearing mice (FIGS. 3B and 3C) but were primarily detected in tumor vasculature (FIGS. 3E and F), and at lower levels in dysplastic skin of these tumor-bearing mice. Together with the immunolocalization analyses of phage homing, the peptide localization data indicate that CGKRK (SEQ ID NO: 6) and CDTRL (SEQ ID NO: 7) home specifically to blood vessels in squamous cell carcinomas and in the dysplastic foci of tumor-bearing mice, but not to vasculature of earlier stage dysplasias in non-tumor bearing mice.

Figure 4:
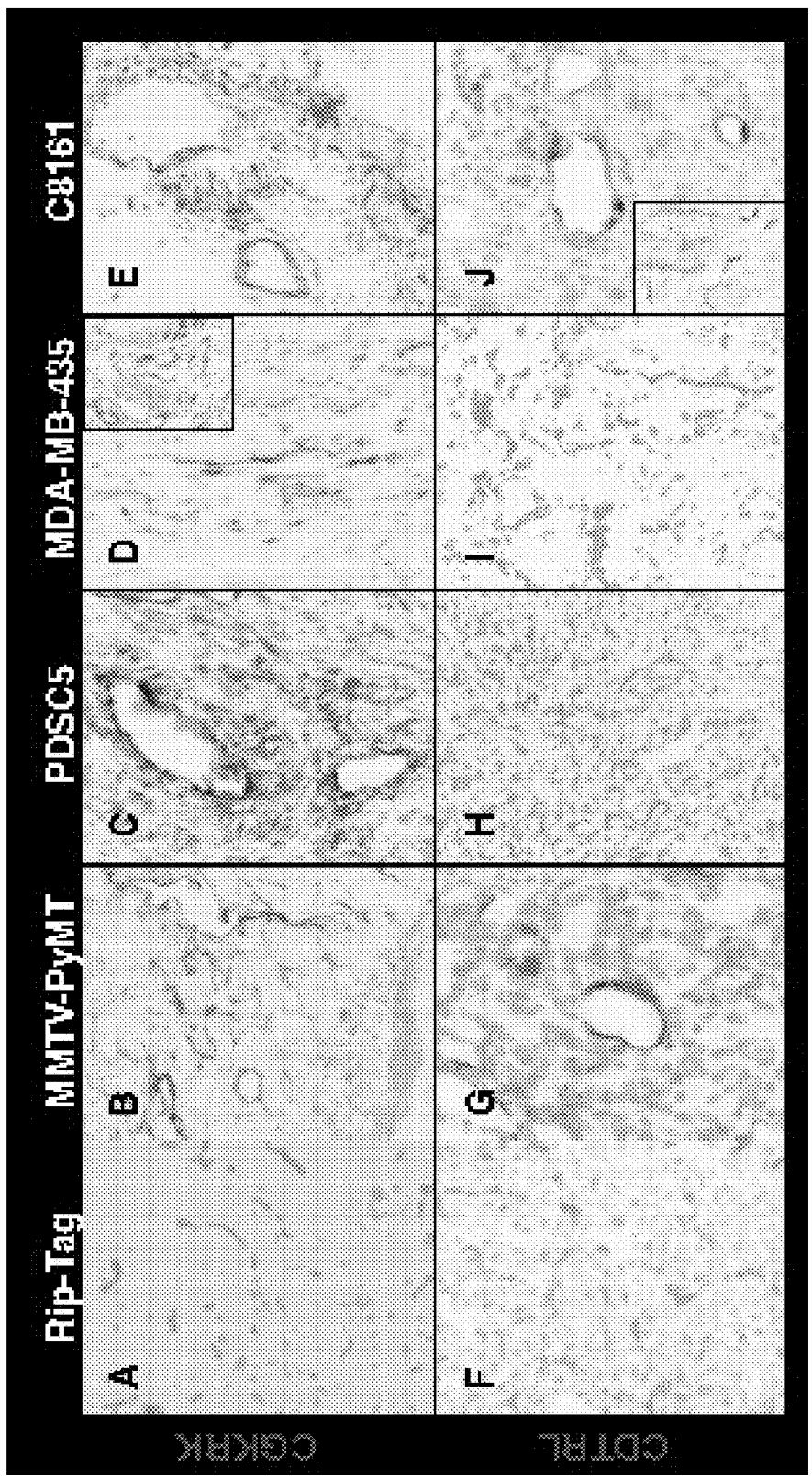
FIG. 4 shows the localization of fluorescein-labeled peptides in various tumors. Mice bearing various tumors were intravenously injected with fluorescein-labeled peptides and examined as in FIG. 3. Tissue sections were stained with Meca-32 and CD31. Fluorescein-CGKRK (SEQ ID NO: 6) (A-E) was detected in four of the five tumor models examined; RIP 1-Tag2 tumors were negative as shown in (A). The CGKRK (SEQ ID NO: 6) peptide was seen in endothelial cells and tumor cells and appeared in both the cytoplasm and nucleus (B-E). Fluorescein-CDTRL (SEQ ID NO: 7) was present in MMTV-PyMT tumors (G) and C8161 xenografts (J). In the C8161 xenografts, the positive cells were CD31-positive cells that were adhering and spreading on the lumenal surface of the blood endothelial cells; the established endothelia were negative (J). Blood vessels in the skin surrounding the C8161 xenograft tumor are also positive for fluorescein-CDTRL (SEQ ID NO: 7) (J inset). In MMTV-PyMT mice, fluorescein-CDTRL (SEQ ID NO: 7) co-localized with CD31 and Meca-32 (G), and also bound to tumor cells within the vessel wall (G). Magnifications shown are 200×.

As further disclosed herein in Example IV, homing selectivity of K14-HPV16 squamous cell cancer-homing peptides, CGKRK (SEQ ID NO: 6) and CDTRL (SEQ ID NO: 7), was analyzed for the ability of these peptides to home to endothelium in tumors of different tissue origins and localized to different anatomical locations. In particular, three subcutaneously implanted tumors and two tumors produced in transgenic animal models were examined for accumulation of fluorescein-labeled peptides following intravenous injection. As shown in FIG. 4, different homing specificities were observed for each peptide in the various tumor microenvironments. In particular, in FIGS. 4A and F, neither peptide CGKRK (SEQ ID NO: 6) nor CDTRL (SEQ ID NO: 7) homed to angiogenic islets (dysplasias) or tumors in the RIP-Tag transgenic mouse model of pancreatic islet cell carcinoma (Hanahan, *Nature* 315:115-122 (1985)), indicating that the binding moieties for these peptides are not present in normal, dysplastic, or pancreatic tumor vasculature. Both CGKRK (SEQ ID NO: 6) and CDTRL (SEQ ID NO: 7) did home to breast carcinomas in the MMTV-PyMT transgenic mouse model (Guy et al., *Mol. Cell. Biol.* 12:954-961 (1992)) as shown in FIGS. 4B and G, and also bound a range of cultured tumor cells in addition to homing to tumor endothelial cells in vivo.

The two peptides that homed to vasculature of malignant skin showed different specificity when assayed for the ability to home to three types of subcutaneously grown transplanted tumors. Fluorescein-CGKRK (SEQ ID NO: 6) homed to cells in each of the three transplant tumors (FIGS. 4C-E), which arose from PDSC5, a K14-HPV16 tumor-derived cell line (FIG. 4C); the MDA-MB-435 human breast cancer line (FIG. 4D; Price et al., *Cancer Res.* 50:717-721 (1990)); or the C8161 human melanoma line (FIG. 4E; Bregman and Meyskens, *Int. J. Cancer* 37:101-107 (1986)). In contrast, the CDTRL (SEQ ID NO: 7) peptide accumulated only in the melanoma xenografts (FIG. 4J) and in the skin overlying the melanoma xenograft tumor (FIG. 4J inset). Furthermore, fluorescein-CGKRK (SEQ ID NO: 6) localized in the cytoplasm and nuclei of vascular cells identified as endothelial cells by their morphology and by immunostaining for CD31 and Meca-32 (see FIG. 4D). These results indicate that cell type or oncogenic stimulus imparts different qualities onto vasculature and the tumor microenvironment, as revealed by differential selective homing patterns.

The discoveries disclosed herein relate to homing peptides and other homing molecules that target different stages of tumor development including, but not limited to, squamous cell carcinogenesis and other dermatological malignancies. Such molecules can distinguish between temporal changes that occur during multi-stage tumorigenesis and provide improved diagnostic tools, including ones affording early detection of pre-malignant lesions and asymptomatic early stage carcinomas. Such homing molecules also can be useful for specifically targeting therapeutics to vasculature of early-stage, pre-malignant lesions or vasculature of a later-stage dysplasia or tumor.

Based on the discoveries discussed above, the present invention provides an isolated peptide or peptidomimetic which has a length of less than 20 residues and includes the amino acid sequence SRPRR (SEQ ID NO: 1) or a peptidomimetic thereof. Such a peptide or peptidomimetic can be cyclic or otherwise conformationally constrained. In particular embodiments, the peptide or peptidomimetic includes the amino acid sequence CSRPRRSEC (SEQ ID NO: 3), CSRPRRSVC (SEQ ID NO: 4) or CSRPRRSWC (SEQ ID NO: 5) or a peptidomimetic thereof. An isolated peptide or peptidomimetic of the invention, such as a conformationally constrained peptide or peptidomimetic can have, without limitation, a length of less than 15 residues or a length of less than 10 residues. A peptide or peptidomimetic of the invention can selectively home to vasculature of pre-malignant dysplastic skin.

The present invention further provides an isolated peptide or peptidomimetic which has a length of less than 90 residues and which includes the amino acid sequence CXSRPRRZC (SEQ ID NO: 2) or a peptidomimetic thereof, where X=0 to 20 independently selected residues and Z=0 to 20 independently selected residues. Such an isolated peptide or peptidomimetic can be cyclic or otherwise conformationally constrained and can include, without limitation, the amino acid sequence CSRPRRSEC (SEQ ID NO: 3), CSRPRRSVC (SEQ ID NO: 4) or CSRPRRSWC (SEQ ID NO: 5) or a peptidomimetic thereof. An isolated peptide or peptidomimetic of the invention can have, without limitation, a length of less than 60 residues, a length of less than 40 residues, or a length of less than 30 residues. Any of such peptides or peptidomimetics including the amino acid sequence CXSRPRRZC (SEQ ID NO: 2) or a peptidomimetic thereof can selectively home to vasculature of pre-malignant dysplastic skin.

Further provided by the present invention is an isolated peptide or peptidomimetic which has a length of less than 20 residues and which includes the amino acid sequence CGKRK (SEQ ID NO: 6) or a peptidomimetic thereof. An isolated peptide or peptidomimetic of the invention, such as a conformationally constrained peptide or peptidomimetic can have, without limitation, a length of less than 15 residues or a length of less than 10 residues. In one embodiment, the isolated peptide or peptidomimetic is cyclic. In another embodiment, the isolated peptide or peptidomimetic is conformationally constrained. Any of such peptides or peptidomimetics including the amino acid sequence CGKRK (SEQ ID NO: 6) or a peptidomimetic thereof can selectively home to vasculature of malignant skin.

Additionally provided herein is an isolated peptide or peptidomimetic which has a length of less than 20 residues and which includes the amino acid sequence CDTRL (SEQ ID NO: 7) or a peptidomimetic thereof. An isolated peptide or peptidomimetic of the invention, such as a conformationally constrained peptide or peptidomimetic can have, for example, a length of less than 15 residues or a length of less than 10 residues. In particular embodiments, the isolated peptide or peptidomimetic is cyclic or conformationally constrained. A peptide or peptidomimetic of the invention including the amino acid sequence CDTRL (SEQ ID NO: 7) or a peptidomimetic thereof can selectively home to vasculature of malignant skin.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

Further provided by the present invention is a conjugate that contains a therapeutic moiety linked to a homing peptide or peptidomimetic which selectively homes to vasculature of pre-malignant dysplastic skin and which includes the amino acid sequence SRPRR (SEQ ID NO: 1) or a conservative variant or peptidomimetic thereof.

Also provided herein is a conjugate containing a therapeutic moiety linked to a homing peptide or peptidomimetic which selectively homes to vasculature of malignant skin and which includes the amino acid sequence CGKRK (SEQ ID NO: 6) or the amino acid sequence CDTRL (SEQ ID NO: 7), or a conservative variant or peptidomimetic of one of these sequences.

The conjugates and methods of the invention disclosed herein below rely on homing molecules. As used herein, the term "molecule" is used broadly to mean a polymeric or non-polymeric organic chemical such as a small molecule drug; a nucleic acid molecule such as an RNA, a cDNA or other DNA, or an oligonucleotide; a peptide or peptidomimetic; or a protein such as an antibody or a growth factor receptor or a fragment thereof such as an Fv, Fd, or Fab fragment of an antibody containing the antigen-binding domain.

The phrase "homing molecule that selectively homes to vasculature of pre-malignant dysplastic skin," as used herein, means any molecule that preferentially localizes in vivo to vasculature of pre-malignant dysplastic skin as compared to vasculature of malignant skin and vasculature of normal skin. Similarly, the phrase "homing peptide or peptidomimetic that selectively homes to vasculature of pre-malignant dysplastic skin" means a peptide or peptidomimetic that preferentially localizes in vivo to vasculature of pre-malignant dysplastic skin as compared to vasculature of malignant skin and vasculature of normal skin. It is understood that a homing molecule that selectively homes to vasculature of pre-malignant dysplastic skin can home to the supporting vasculature of a variety of dysplastic lesions in addition to dysplastic skin, or can exhibit preferential homing to vasculature of pre-malignant dysplastic lesions in a subset of tissue types including dysplastic skin, or can exhibit significant homing exclusively to vasculature of pre-malignant dysplastic skin.

Selective homing of a homing molecule that selectively homes to vasculature of pre-malignant dysplastic skin generally is characterized by at least a two-fold greater localization within vasculature of pre-malignant dysplastic skin as compared to vasculature of malignant skin and normal skin vasculature. Such a homing molecule can be characterized, for example, by 5-fold, 10-fold, 20-fold or more greater localization within vasculature of pre-malignant dysplastic skin as compared to vasculature of malignant skin and normal skin vasculature. As discussed above, it is understood that a homing molecule that selectively homes to vasculature of premalignant dysplastic skin can home, in part, to vasculature of one or more other dysplastic tissues.

The phrase "homing molecule that selectively homes to vasculature of malignant skin," as used herein, means any molecule that preferentially localizes in vivo to vasculature of malignant skin or later-stage dysplasias as compared to vasculature of early-stage pre-malignant dysplasias and vasculature of normal skin. Similarly, the phrase "homing peptide or peptidomimetic that selectively homes to vasculature of malignant skin" means a peptide or peptidomimetic that preferentially localizes in vivo to vasculature of malignant skin or later-stage dysplasias as compared to vasculature of early-stage pre-malignant dysplasias and vasculature of normal skin. One skilled in the art understands that a homing molecule that selectively homes to vasculature of malignant skin can home to the supporting vasculature of a variety of different malignancies in addition to malignant skin, or can exhibit preferential homing to vasculature of a subset of malignancies including malignant skin, or can exhibit significant homing exclusively to vasculature of malignant skin.

Selective homing of a homing molecule that selectively homes to vasculature of malignant skin generally is characterized by at least a two-fold greater localization within vasculature of malignant skin or later-stage dysplasias as compared to vasculature of early-stage pre-malignant dysplastic skin and normal skin. Such a homing molecule can be characterized, for example, by 5-fold, 10-fold, 20-fold or more greater localization within vasculature of malignant skin or later-stage dysplasias as compared to vasculature of early-stage pre-malignant dysplastic skin and normal skin. As discussed above, it is understood that a homing molecule that selectively homes to vasculature of malignant skin can additionally localize to vasculature or tumor cells of one or more other malignant tissues in addition to selectively homing to malignant skin.

The present invention also provides a conjugate containing a homing peptide or peptidomimetic that includes an amino acid sequence which is a conservative variant, for example, of the amino acid sequence SRPRR (SEQ ID NO: 1). As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

Further provided herein is a multivalent conjugate containing a moiety linked to at least two homing peptides or peptidomimetics which each selectively home to vasculature of pre-malignant dysplastic skin and which include the amino acid sequence SRPRR (SEQ ID NO: 1) or a conservative variant or peptidomimetic thereof. Such a multivalent conjugate can include, without limitation, at least 10 homing peptides or peptidomimetics or at least 100 homing peptides or peptidomimetics. In a multivalent conjugate of the invention, the homing peptides or peptidomimetics can optionally be cyclic or otherwise conformationally constrained, and can be linked to any of a variety of moieties such as a phage moiety.

In one embodiment, the invention provides a multivalent conjugate containing a moiety linked to at least two homing peptides or peptidomimetics which each selectively home to vasculature of pre-malignant dysplastic skin and which each independently include the amino acid sequence CXSRPRRZC (SEQ ID NO: 2) or a conservative variant or peptidomimetic thereof, where X=0 to 20 independently selected residues and where Z=0 to 20 independently selected residues. In further embodiments, such a multivalent conjugate includes at least ten homing peptides or peptidomimetics that each selectively home to vasculature of pre-malignant dysplastic skin, or at least 100 homing peptides or peptidomimetics that each selectively home to vasculature of pre-malignant dysplastic skin. Moieties useful in a multivalent conjugate of the invention include but are not limited to phage moieties. In further embodiments, the invention provides a multivalent conjugate containing a moiety linked to at least two, at least ten, or at least 100, homing peptides or peptidomimetics which each selectively home to vasculature of pre-malignant dysplastic skin and which each independently include the amino acid sequence CSRPRRSEC (SEQ ID NO: 3) or a conservative variant or peptidomimetic thereof. In other embodiments, the invention provides a multivalent conjugate containing a moiety linked to at least two, at least ten, or at least 100, homing peptides or peptidomimetics which each selectively home to vasculature of pre-malignant dysplastic skin and which each independently include the amino acid sequence CSRPRRSVC (SEQ ID NO: 4) or a conservative variant or peptidomimetic thereof. In still further embodiments, the invention provides a multivalent conjugate containing a moiety linked to at least two, at least ten, or at least 100, homing peptides or peptidomimetics which each selectively home to vasculature of pre-malignant dysplastic skin and which each independently include the amino acid sequence CSRPRRSWC (SEQ ID NO: 5) or a conservative variant or peptidomimetic thereof.

Also provided by the invention is a multivalent conjugate containing a moiety linked to at least two homing peptides or peptidomimetics which each selectively home to vasculature of malignant skin and which include the amino acid sequence CGKRK (SEQ ID NO: 6) or CDTRL (SEQ ID NO: 7) or a conservative variant or peptidomimetic thereof. Such a multivalent conjugate can include, without limitation, at least 10 homing peptides or peptidomimetics or at least 100 homing peptides or peptidomimetics. In a multivalent conjugate of the invention, the homing peptides or peptidomimetics can optionally be cyclic or otherwise conformationally constrained, and can be linked to any of a variety of moieties such as a phage moiety.

A multivalent conjugate of the invention containing multiple homing molecules can include, for example, two or more, three or more, five or more, ten or more, twenty or more, thirty or more, forty or more, fifty or more, 100 or more, 200 or more, 300 or more, 400 or more, 500 or more or 1000 or more homing molecules. In one embodiment, the homing molecules have an identical amino acid sequence. In another embodiment, the multivalent conjugate includes homing molecules having non-identical amino acid sequences. Moieties useful in a multivalent conjugate of the invention include, without limitation, phage, retroviruses, adenoviruses, adeno-associated viruses and other viruses, cells, liposomes, polymeric matrices, non-polymeric matrices or particles such as gold particles, microdevices and nanodevices, and nano-scale semiconductor materials.

Liposomes consisting, without limitation, of phospholipids or other lipids, are nontoxic, physiologically acceptable and metabolizable carriers that are readily made to be incorporated into a conjugate of the invention (Gregoriadis, *Liposome Technology*, Vol. 1 (CRC Press, Boca Raton, Fla. (1984)). It is understood that the liposome or other polymeric matrix additionally can include one or more other components if desired, such as, without limitation, one or any combination of therapeutic agents, anti-angiogenic agents or cytotoxic agents.

As disclosed herein, peptide CSRPRRSEC (SEQ ID NO: 3) recognizes a target "receptor" which is expressed in vasculature of pre-malignant skin dysplasias but which is essentially absent or inaccessible for binding via the circulation in vasculature of normal skin and vasculature of squamous cell carcinomas. The cell surface and cell-type selective expression of the target receptor form the basis for the selective homing activity of peptide SEQ ID NO: 3, 4 and 5 and related peptides, peptidomimetics and other molecules. Based on this discovery, it is also clear that molecules structurally unrelated to SEQ ID NO: 3, 4 or 5 or the generic sequences SEQ ID NOS: 1 and 2 but which bind the same receptor also have the same characteristic of selectively homing to vasculature of pre-malignant dysplastic skin and other pre-malignant dysplastic tissues. Such molecules can be identified by the ability to specifically bind to, or to compete with SEQ ID NO: 3, 4, 5 or a related peptide such as a SRPRR (SEQ ID NO: 1)-containing peptide for specific binding to, cells expressing a cognate receptor for SEQ ID NO: 3 such as pre-malignant dysplastic skin cells from K14-HPV16 mice at 4-6 months of age as described further below. Selective homing to vasculature of pre-malignant dysplastic skin readily can be confirmed using in vivo panning as disclosed herein in Example I (see, also, U.S. Pat. No. 5,622,699).

A homing molecule of the invention specifically binds the indicated cognate receptor. As used herein, the term "specifically binds" or "specifically binding" means binding that is measurably different from a non-specific interaction. Specific binding can be measured, for example, by determining binding of a molecule compared to binding of a control molecule, which generally is a molecule of similar structure that does not have binding activity. In this case, specific binding is indicated if the molecule has measurably higher affinity for cells expressing the cognate receptor, for example, than for cells that do not express the cognate receptor. As a non-limiting example, peptides SEQ ID NOS: 6 and 7 bind a range of cultured tumor cells in vivo, including, for example, HL-60 human leukemia cells, MDA-MB-435 human breast carcinomas and PDSC5 squamous cell carcinomas. Specificity of binding can be determined, for example, by competitive inhibition of the binding of a known binding molecule such as SEQ ID NO: 3 to identify molecules that selectively home to vasculature of pre-malignant dysplastic skin, or by competitive inhibition of the binding of a known binding molecule such as SEQ ID NO: 6 or 7 to identify molecules that selectively home to vasculature of malignant skin.

The term "specifically binding," as used herein, includes both low and high affinity specific binding. Specific binding can be exhibited, for example, by a low affinity homing molecule having a Kd of at least about $10^{-4}$ M. For example, if the cognate receptor has more than one binding site, a homing molecule having low affinity can be useful for targeting, for example, vasculature of pre-malignant dysplastic skin or vasculature of malignant skin. Specific binding also can be exhibited by a high affinity homing molecule, for example, a homing molecule having a Kd of at least about $10^{-5}$ M. Such a molecule can have, for example, a Kd of at least about $10^{-6}$ M, at least about $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful and are encompassed by the invention. Low affinity homing molecules are useful in targeting, for example, multivalent conjugates such as viruses and other particles. High affinity homing molecules are useful in targeting, for example, multivalent and univalent conjugates.

Thus, the invention further provides a conjugate which contains a therapeutic moiety linked to a homing molecule which selectively homes to vasculature of pre-malignant dysplastic skin and which specifically binds a cognate receptor for CSRPRRSEC (SEQ ID NO: 3). In one embodiment, such a conjugate contains a homing molecule which is not an antibody or antigen-binding fragment thereof. In another embodiment, the homing molecule is a kallikrein 9-binding molecule. In further embodiments, the peptide or peptidomimetic portion of the conjugate has a length of at most 200 residues, or a length of at most 50 residues.

Also provided by the invention is a conjugate which contains a detectable moiety linked to a homing molecule which selectively homes to vasculature of pre-malignant dysplastic skin and which specifically binds a cognate receptor for CSRPRRSEC (SEQ ID NO: 3). Such a conjugate can contain, for example, a homing molecule which is not an antibody or antigen-binding fragment thereof. In another embodiment, the homing molecule is a kallikrein 9-binding molecule. In further embodiments, the peptide or peptidomimetic portion of the conjugate has a length of at most 200 residues, or a length of at most 50 residues. A variety of detectable moieties are useful in a conjugate of the invention including, but not limited to, radionuclides and fluorescent labels.

A homing molecule which specifically binds a cognate receptor for CSRPRRSEC (SEQ ID NO: 3) can be, without limitation, a homing peptide or peptidomimetic. In one embodiment, a conjugate of the invention contains a homing peptide or peptidomimetic which selectively homes to vasculature of pre-malignant dysplastic skin and which includes the amino acid sequence SRPRR (SEQ ID NO: 1) or a conservative variant or peptidomimetic of this sequence. Such a homing peptide or peptidomimetic can include, for example, the amino acid sequence SEQ ID NO: 1, or a peptidomimetic thereof. In another embodiment, a conjugate of the invention contains a homing peptide or peptidomimetic which selectively homes to vasculature of pre-malignant dysplastic skin and which includes the amino acid sequence SEQ ID NO: 2, where X=0 to 20 independently selected residues and where Z=0 to 20 independently selected residues, or a conservative variant or peptidomimetic thereof. Such a homing peptide or peptidomimetic can include, for example, the amino acid sequence SEQ ID NO: 2, where X=0 to 20 independently selected residues and where Z=0 to 20 independently selected residues, or a peptidomimetic of this sequence.

There further is provided herein a method of directing a moiety to vasculature of a pre-malignant dysplastic tissue in a subject by administering to the subject a conjugate that contains a moiety linked to a homing molecule which selectively homes to vasculature of pre-malignant dysplastic skin and which specifically binds a cognate receptor for CSRPRRSEC (SEQ ID NO: 3), thereby directing the moiety to vasculature of the pre-malignant dysplastic tissue. In one embodiment, the invention provides a method of directing a moiety to vasculature of a pre-malignant dysplastic tissue using a homing molecule other than an antibody or antigen-binding fragment thereof.

The present invention further provides a method of imaging vasculature of a pre-malignant dysplastic tissue by administering to the subject a conjugate containing a detectable moiety linked to a homing molecule which selectively homes to vasculature of pre-malignant dysplastic skin and which specifically binds a cognate receptor for CSRPRRSEC (SEQ ID NO: 3) and detecting the conjugate, thereby imaging vasculature of the pre-malignant dysplastic tissue. In one embodiment, the invention provides a method of imaging vasculature of a pre-malignant dysplastic tissue using a homing molecule other than an antibody or antigen-binding fragment thereof.

Further provided herein is a method of reducing the risk of progression to a malignancy in a subject by administering to the subject a conjugate containing a therapeutic moiety linked to a homing molecule which selectively homes to vasculature of pre-malignant dysplastic skin and which specifically binds a cognate receptor for CSRPRRSEC (SEQ ID NO: 3), thereby diminishing vasculature of a pre-malignant dysplastic tissue and reducing the risk of progression to the malignancy. In one embodiment, such a method of reducing the risk of progression to a malignancy is practiced with a homing molecule other than an antibody or antigen-binding fragment thereof.

Moieties useful in the methods of the invention are discussed further below and include, without limitation, therapeutic and detectable moieties. Therapeutic moieties which can be directed to vasculature of a pre-malignant dysplastic lesion include, but are not limited to, anti-angiogenic agents such as those effective against pre-malignant vasculature, and cytotoxic agents. Moieties which can be directed to vasculature of a pre-malignant dysplastic lesion further encompass, without limitation, detectable moieties such as fluorescent labels and radionuclides, including but not limited to, indium-111, technetium-99, carbon-11, and carbon-13.

In particular embodiments, the conjugates and methods of the invention are practiced with a homing molecule which selectively homes to vasculature of pre-malignant dysplastic skin and which specifically binds a cognate receptor for CSRPRRSEC (SEQ ID NO: 3), where the homing molecule does not include any of the amino acid sequences shown in Table 1 below. In further embodiments, the conjugates and methods of the invention are practiced with a homing molecule which selectively homes to vasculature of pre-malignant dysplastic skin and which specifically binds a cognate receptor for CSRPRRSEC (SEQ ID NO: 3), where the homing molecule does not include any of the amino acid sequences shown in Table 1, or conservative variants thereof.

TABLE I

| Sequence | SEQ ID NO |
|---|---|
| CYADCEGTCGMVC | (18) |
| CWNICPGGCRALC | (19) |
| GPGCEEECQPAC | (20) |
| CKGTCVLGCSEEC | (21) |
| CSTLCGLRCMGTC | (22) |
| CMPRCGVNCKWAC | (23) |
| CVGACDLKCTGGC | (24) |
| CVALCREACGEGC | (25) |
| CSSGCSKNCLEMC | (26) |
| CGRPCRGGCAASC | (27) |
| CQGGCGVSCPIFC | (28) |
| CAVRCDGSCVPEC | (29) |
| CGFGCSGSCQMQC | (30) |
| CRVVCADGCRFIC | (31) |
| CTMGCTAGCAFAC | (32) |
| CEGKCGLTCECTC | (33) |
| CNQGCSGSCDVMC | (34) |
| CASGCSESCYVGC | (35) |
| CGGGCQWGCAGEC | (36) |
| CSVRCKSVCIGLC | (37) |
| CPSNCVALCTSGC | (38) |
| CVEGCSSGCGPGC | (39) |
| CRVVCADGCRLIC | (40) |
| CSTLCGLRCMGTC | (41) |
| CFTFCEYHCQLTC | (42) |

Parentheses contain SEQ ID NO:.

Homing molecules which selectively home to vasculature of pre-malignant dysplastic skin and which selectively bind a cognate receptor for SEQ ID NO: 3 include, but are not limited to, kallikrein 9 analogs such as small molecule, peptide and peptidomimetic analogs. Kallikrein 9 (KLK9 or KLK-L3) is a member of the kallikrein gene family, a subfamily of serine proteases with a conserved catalytic triad (histidine, aspartic acid and serine). At least 14 human kallikrein-like genes have been identified, including the prognostic marker prostate-specific antigen (PSA), and all colocalize to the same region of chromosome 13 (q13.3-13.4). Members of the kallikrein gene family generally have five coding exons and exhibit 30-80% sequence homology at the DNA and amino acid levels, with kallikrein 9 exhibiting 38% and 33% amino acid identity with the KLK-L2 and KLK-L1 proteins, respectively. Many members of the kallikrein gene family, including kallikrein 9, are upregulated by steroid hormones and further may be downregulated in breast or other cancers or have anti-angiogenic activity (Diamandis et al., *Trends Endocrin. Metab.* 11: 54-60 (2000)).

Kallikrein 9 is mainly expressed in skin, thymus, trachea, cerebellum and spinal cord as well as brain, salivary gland, mammary gland, ovary and prostate. (Yousef et al., *Genomics* 65:184-194 (2000); Yousef et al., *Anticancer Res.* 19:2843-2852 (1999)). Lower levels of kallikrein 9 expression are observed in fetal brain, stomach, lung, thyroid, placenta, liver, small intestine and bone marrow (Yousef et al., supra, 2000). As indicated above, kallikrein 9 is hormonally regulated, for example, by the steroids estrogen and progestin in ovarian and breast cancer cell lines. Furthermore, in ovarian tumors, kallikrein 9 expression is an independent favorable prognostic marker; patients with KLK9-positive tumors have substantially increased progression-free survival as well as substantially increased overall survival (Yousef et al., *Cancer Res.* 61: 7811-7817 (2001)).

As disclosed herein, the Cys220 to Arg225 portion of human kallikrein 9 ($C_{220}SRPRR_{225}$ (SEQ ID NO: 17); Yousef and Diamandis, *Genomics* 65:184-194 (2000)) is homologous to the homing peptide CSRPRRSEC (SEQ ID NO: 3). The Cys200 to Arg225 sequence is also conserved in the mouse homolog of kallikrein 9 (RIKEN clone 1200016C12; Kawai et al., *Nature* 409:685-690 (2001)) and is present in homing peptides CSRPRRSVC (SEQ ID NO: 4) and CSRPRRSWC (SEQ ID NO: 5), which, like CSRPRRSEC (SEQ ID NO: 3), selectively home to vasculature of pre-malignant dysplastic skin. Structural studies have shown that the Cys200 to Arg225 sequence of human kallikrein 9 forms a loop that defines substrate specificities in the kallikreins by contributing to a portion of the entrance to the active site; this loop is highly variable among kallikreins and other trypsin-family members (Gomis-Ruth et al., *J. Biol. Chem.* 277: 27273-27281 (2002)). In kallikrein 9 and other kallikreins, Cys200 forms a disulfide bond with Cys190, the cysteine next to the active site nucleophile Ser195; the loop is closed with a kink introduced by invariant Pro226. Similarly, a disulfide bond is present in CSRPRRSEC (SEQ ID NO: 3), CSRPRRSVC (SEQ ID NO: 4) and CSRPRRSWC (SEQ ID NO: 5), conformationally constraining these homing peptides, which can act as analogs of kallikrein 9.

As used herein, the term "kallikrein 9 analog" means a molecule that specifically binds to a naturally occurring kallikrein 9-binding molecule which is expressed or localized at higher levels on angiogenic endothelia of pre-malignant dysplastic skin lesions than on angiogenic endothelia of squamous carcinomas. Such a kallikrein 9 analog can be, without limitation, a small molecule, peptide, peptidomimetic or protein that specifically binds to a naturally occurring kallikrein 9-binding molecule, which is a kallikrein 9 substrate or inhibitor. In one embodiment, the kallikrein 9 analog specifically binds to a substrate which is a precursor to an anti-angiogenic molecule such as prostate serum antigen (PSA). In another embodiment, the kallikrein 9 analog specifically binds to a substrate which is a pro-angiogenic factor inactivated upon cleavage by kallikrein 9. Kallikrein 9 analogs include, but are not limited to, peptides and peptidomimetics such as SEQ ID NO: 1; SEQ ID NO: 2, where X=0 to 20 independently selected residues and where Z=0 to 20 independently selected residues; SEQ ID NO: 3; SEQ ID NO: 4; and SEQ ID NO: 5, and conservative variants and peptidomimetics of any of these sequences.

As further disclosed herein, peptides CGKRK (SEQ ID NO: 6) and CDTRL (SEQ ID NO: 7) each recognize a target "receptor" which is expressed in vasculature of malignant skin and breast carcinomas but which is essentially absent or inaccessible for binding via the circulation in normal skin and other normal tissues and present at reduced or variable levels in early stage dysplasias. The cell surface and cell-type selective expression of the target receptor form the basis for the selective homing activity of peptides SEQ ID NOS: 6 and 7 and related peptides, peptidomimetics and other molecules. From the above, it is clear to one skilled in the art that molecules structurally unrelated to SEQ ID NO: 6 or 7 but which bind one of the same cognate receptors also have the same characteristic of selectively homing to vasculature of malignant tissues such as vasculature of malignant skin. Such molecules can be identified by the ability to specifically bind to, or to compete with SEQ ID NO: 6 or 7 for specific binding to, cells expressing the cognate receptor for SEQ ID NO: 6 or SEQ ID NO: 7, such as MDA-MB-435 human breast cancer cells, C8161 human melanoma cells, HL-60 human leukemia cells and PDSC5 squamous cell carcinomas. Selective homing to vasculature of malignant tissues readily can be confirmed using in vivo panning (see Example II and U.S. Pat. No. 5,622,699).

The invention further provides a conjugate which contains a therapeutic moiety linked to a homing molecule which selectively homes to vasculature of malignant skin and which specifically binds a cognate receptor for CGKRK (SEQ ID NO: 6) or CDTRL (SEQ ID NO: 7). In one embodiment, such a conjugate contains a homing molecule which is not an antibody or antigen-binding fragment thereof. In further embodiments, the peptide or peptidomimetic portion of the conjugate has a length of at most 200 residues, or a length of at most 50 residues.

Also provided herein is a conjugate which contains a detectable moiety linked to a homing molecule which selectively homes to vasculature of malignant skin and which specifically binds a cognate receptor for CGKRK (SEQ ID NO: 6) or CDTRL (SEQ ID NO: 7). In one embodiment, such a conjugate contains a homing molecule which is not an antibody or antigen-binding fragment thereof. In further embodiments, the peptide or peptidomimetic portion of the conjugate has a length of at most 200 residues, or a length of at most 50 residues. Detectable moieties useful in a conjugate of the invention include, without limitation, radionuclides and fluorescent labels.

A homing molecule which specifically binds a cognate receptor for CGKRK (SEQ ID NO: 6) or CDTRL (SEQ ID NO: 7) can be, without limitation, a homing peptide or peptidomimetic. In one embodiment, a conjugate of the invention contains a homing peptide or peptidomimetic which selectively homes to vasculature of malignant skin and which is cyclic or otherwise conformationally constrained. In another embodiment, a conjugate of the invention contains a homing peptide or peptidomimetic which selectively homes to vasculature of malignant skin and which includes the amino acid sequence CGKRK (SEQ ID NO: 6) or a conservative variant or peptidomimetic of this sequence. Such a homing peptide or peptidomimetic can include, for example, the amino acid sequence SEQ ID NO: 6, or a peptidomimetic thereof. In another embodiment, a conjugate of the invention contains a homing peptide or peptidomimetic which selectively homes to vasculature of malignant skin and which includes the amino acid sequence CDTRL (SEQ ID NO: 7), or a conservative variant or peptidomimetic thereof. Such a homing peptide or peptidomimetic can contain, for example, the amino acid sequence SEQ ID NO: 7 or a peptidomimetic thereof.

Also provided herein is a method of directing a moiety to vasculature of a malignant tissue in a subject by administering to the subject a conjugate containing a moiety linked to a homing molecule which selectively homes to vasculature of malignant skin and which specifically binds a cognate receptor for SEQ ID NO: 6 or SEQ ID NO: 7, thereby directing the moiety to vasculature of the malignant tissue. In one embodiment, a method of the invention for directing a moiety to vasculature of a malignant tissue in a subject is practiced with a homing molecule other than an antibody or antigen-binding fragment thereof.

Also provided herein is a method of imaging vasculature of a malignant tissue by administering to the subject a conjugate containing a detectable moiety linked to a homing molecule which selectively homes to vasculature of malignant skin and which specifically binds a cognate receptor for SEQ ID NO: 6 or SEQ ID NO: 7; and detecting the conjugate, thereby imaging vasculature of the malignant tissue. The invention provides, in one embodiment, a method of imaging vasculature of a malignant tissue using a homing molecule other than an antibody or antigen-binding fragment thereof.

In addition, there is provided herein a method of treating a cancer in a subject by administering to the subject a conjugate containing a therapeutic moiety linked to a homing molecule which selectively homes to vasculature of malignant skin and which specifically binds a cognate receptor for SEQ ID NO: 6 or SEQ ID NO: 7, thereby directing the therapeutic moiety to vasculature of the cancer and treating the cancer. In one embodiment, the invention provides a method of treating cancer in a subject using a homing molecule other than an antibody or antigen-binding fragment thereof.

The present invention further provides a method of staging tumor progression in a subject having or suspected of having a pre-malignant lesion or tumor by administering to the subject a conjugate containing a detectable moiety linked to (i) a homing molecule which selectively homes to vasculature of pre-malignant dysplastic skin and which specifically binds a cognate receptor for CSRPRRSEC (SEQ ID NO: 3), or (ii) a homing molecule which selectively homes to vasculature of malignant skin and which specifically binds a cognate receptor for CGKRK (SEQ ID NO: 6) or CDTRL (SEQ ID NO: 7); and detecting the conjugate, where detection of the conjugate containing a homing molecule which selectively homes to vasculature of pre-malignant dysplastic skin indicates a pre-malignant stage of tumor progression in the subject and where detection of the conjugate containing a homing molecule which selectively homes to vasculature of malignant skin indicates a malignant stage of tumor progression in the subject. In one embodiment, such a method of staging tumor progression is practiced with a homing molecule other than an antibody or antigen-binding fragment thereof.

A variety of moieties can be linked to a homing molecule that selectively homes to vasculature of malignant skin in a method of the invention. Such moieties, which are discussed further below include, without limitation, therapeutic and detectable moieties. Therapeutic moieties which can be directed to vasculature of a malignant tissue include, but are not limited to, anti-angiogenic agents such as those effective against tumor vasculature, and cytotoxic agents. Moieties which can be directed to vasculature of a malignant tissue and which can be useful in staging tumor progression further encompass, without limitation, detectable moieties such as fluorescent labels and radionuclides including, but not limited to, indium-111, technetium-99, carbon-11, and carbon-13.

In particular embodiments, the conjugates and methods of the invention are practiced with a homing molecule which selectively homes to vasculature of malignant skin and which specifically binds a cognate receptor for SEQ ID NO: 6 or SEQ ID NO: 7, where the homing molecule does not include any of the amino acid sequences shown in Table 1 above. In further embodiments, the conjugates and methods of the invention are practiced with a homing molecule which selectively homes to vasculature of malignant skin and which specifically binds a cognate receptor for SEQ ID NO: 6 or SEQ ID NO: 7, where the homing molecule does not include any of the amino acid sequences shown in Table 1, or conservative variants thereof.

As set forth above, in particular embodiments, several conjugates of the invention include a homing molecule that is not an antibody or antigen-binding fragment thereof. "Antibody" is an art-recognized term that refers to a peptide or polypeptide containing one or more complementarity determining regions (CDRs). See, for example, Borrabaeck, *Antibody Engineering* 2nd Edition, Oxford University Press, New York (1995).

The invention further provides a multivalent conjugate contain, for example, a liposome or other polymeric matrix or moiety linked to at least two homing molecules which each selectively homes to vasculature of pre-malignant dysplastic skin and which specifically bind a cognate receptor for SEQ ID NO: 3. Additional multivalent conjugates of the invention provided herein include a liposome or other polymeric matrix or moiety linked to at least two homing molecules which each selectively homes to vasculature of malignant skin and which specifically bind a cognate receptor for SEQ ID NO: 6. Still further multivalent conjugates provided herein contain, for example, a liposome or other polymeric matrix or moiety linked to at least two homing molecules which each selectively homes to vasculature of malignant skin and which specifically bind a cognate receptor for SEQ ID NO: 7. If desired, the liposome or other polymeric matrix can be linked to at least ten or at least 100 of such homing molecules. Any of a variety of moieties can be useful in such a multivalent conjugate including, but not limited to, those described herein above.

The peptides and peptidomimetics and homing peptides and peptidomimetics of the invention, including the bifunctional and multivalent peptides and peptidomimetics disclosed herein below, can have a variety of lengths. A peptide or peptidomimetic of the invention can have, for example, a relatively short length of less than six, seven, eight, nine, ten, 12, 15, 20, 25, 30, 35, 40, 45, 50, 60, 70 or 80 residues. A peptide or peptidomimetic of the invention also can be useful in the context of a significantly longer sequence as described further below. As used herein, the term "residue" refers to amino acids or analogs thereof. It is understood that a peptide containing, for example, the amino acid sequence SEQ ID NO: 1 includes the specified amino acids as a contiguous sequence not separated by other amino acids.

In other embodiments, the peptide or peptidomimetic portion of the conjugate has a defined length. The peptide or peptidomimetic portion of the conjugate can have, for example, a length of at most 10, 20, 30, 40, 50, 100, 150, 200, 250, 300, 400, 500, 600, 700, 800, 900, 1000 or 2000 residues. It is understood that the term "peptide or peptidomimetic portion of the conjugate" means the total number of residues in the homing peptide or peptidomimetic and any contiguous protein, peptide or peptidomimetic, such as a therapeutic protein or pro-apoptotic peptide.

As disclosed herein, a homing peptide or peptidomimetic of the invention can maintain homing activity in the context of a significantly longer sequence. As a non-limiting example, the 9-mer peptide CSRPRRSRC (SEQ ID NO: 3) maintained the ability to home when fused to a phage coat protein, confirming that a peptide of the invention can have selective homing activity when embedded in a larger protein sequence. Thus, the invention further provides a chimeric protein containing a peptide or peptidomimetic of the invention, or a homing peptide or peptidomimetic of the invention, fused to a heterologous protein. In one embodiment, the invention provides a chimeric protein containing a homing peptide or peptidomimetic which selectively homes to vasculature of pre-malignant dysplastic skin and which specifically binds a cognate receptor for CSRPRRSEC (SEQ ID NO: 3) fused to a heterologous protein. Such a heterologous protein can be, without limitation, a heterologous protein having a therapeutic activity, or an antibody or antigen-binding fragment thereof. In other embodiments, the invention provides a chimeric protein in which a homing peptide or peptidomimetic containing the amino acid sequence SRPRR (SEQ ID NO: 1), CXSRPRRZC (SEQ ID NO: 2), CSRPRRSEC (SEQ ID NO: 3), CSRPRRSVC (SEQ ID NO: 4) or CSRPRRSWC (SEQ ID NO: 5) or a conservative variant or peptidomimetic of one or these sequences, is fused to a heterologous protein.

The invention additionally provides a chimeric protein containing a homing peptide or peptidomimetic which selectively homes to vasculature of malignant skin and which specifically binds a cognate receptor for CGKRK (SEQ ID NO: 6) or CDTRL (SEQ ID NO: 7) fused to a heterologous protein. Such a heterologous protein can be, without limitation, a heterologous protein having a therapeutic activity, or an antibody or antigen-binding fragment thereof. In particular embodiments, the invention provides a chimeric protein in which a homing peptide or peptidomimetic containing the amino acid sequence CGKRK (SEQ ID NO: 6) or CDTRL (SEQ ID NO: 7) or a conservative variant or peptidomimetic of one or these sequences, is fused to a heterologous protein.

The term "heterologous," as used herein in reference to a protein fused to a homing peptide or peptidomimetic of the invention, means a protein derived from a source other than the gene encoding the fused homing peptide or upon which the fused homing peptidomimetic is derived. A chimeric protein of the invention can have a variety of lengths including, but not limited to, up to 100, 200, 300, 400, 500, 800, 1000 or 2000 residues or more.

The invention also provides bifunctional peptides. The invention provides, for example, a bifunctional peptide which contains a homing peptide that selectively homes to vasculature of pre-malignant dysplastic skin fused to a second peptide having a separate function, and further provides a bifunctional peptide which contains a homing peptide that selectively homes to vasculature of malignant skin fused to a second peptide having a separate function. Such bifunctional peptides have at least two functions conferred by different portions of the peptide and can, for example, display anti-angiogenic activity or pro-apoptotic activity in addition to selective homing activity. As non-limiting examples, the invention provides bifunctional peptides such as SRPRR-GG-$_D$(KLAKLAK)$_2$, CSRPPRSEC-GG-$_D$(KLAKLAK)$_2$, CGKRK-GG-$_D$(KLAKLAK)$_2$ or CDTRL-GG-$_D$(KLAK-LAK)$_2$. In such peptides, the SRPRR (SEQ ID NO: 1), CSR-PPRSEC (SEQ ID NO: 3), CGKRK (SEQ ID NO: 6) or CDTRL (SEQ ID NO: 7) portion exhibits selective homing activity, while the $_D$(KLAKLAK)$_2$ portion exhibits pro-apoptotic activity.

It is understood that a homing molecule useful in the invention can be, without limitation, a homing peptide or peptidomimetic. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids, and have an activity such as the selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, but not limited to, peptide-like molecules which contain a constrained amino acid, a non-peptide component that mimics peptide secondary structure, or an amide bond isostere. A peptidomimetic that contains a constrained, non-naturally occurring amino acid can include, without limitation, an α-methylated amino acid; α,α-dialkylglycine or α-aminocycloalkane carboxylic acid; an N$^α$—C$^α$ cyclized amino acid; an N$^α$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—C$^δ$ or C$^α$-C$^δ$ cyclized amino acid; a substituted proline or another amino acid mimetic. A peptidomimetic which mimics peptide secondary structure can contain, without limitation, a nonpeptidic β-turn mimic; γ-turn mimic; mimic of β-sheet structure; or mimic of helical structure, each of which is well known in the art. As non-limiting examples, a peptidomimetic also can be a peptide-like molecule which contains an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro, Calif.), contains about 100,000 compounds that are commercially available and also can be searched to identify potential peptidomimetics of a peptide of the invention, for example, with activity in selectively homing to pre-malignant dysplastic skin or to malignant skin.

A homing peptide, peptidomimetic or molecule useful in the invention can optionally be cyclic or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include, yet are not limited to, cyclization.

As used herein in reference to a peptide or peptidomimetic, the term cyclic refers to a structure including an intramolecular bond between two non-adjacent amino acids or amino acid analogs. The cyclization can be effected through a covalent or non-covalent bond. Intramolecular bonds include, but are not limited to, backbone to backbone, side-chain to backbone, and side-chain to side-chain bonds. Methods of cyclization include, without limitation, formation of a disulfide bond between the side-chains of non-adjacent amino acids or amino acid analogs; formation of a lactam bond, for example, between a side-chain group of one amino acid or analog thereof to the N-terminal amine of the amino-terminal amino acid or analog; and formation of lysinonorleucine and dityrosine bonds.

The conjugates and methods of the invention can be practiced with a homing antibody or antigen-binding fragment thereof which selectively homes to vasculature of pre-malignant dysplastic skin or which selectively homes to vasculature of malignant skin. As used herein, the term "antibody" is used in its broadest sense to include polyclonal and monoclonal antibodies, as well as polypeptide fragments of antibodies that retain binding activity for the respective cognate receptor of at least about $1\times10^5$ M$^{-1}$. One skilled in the art understands that antibody fragments including, without limitation, Fab, F(ab')$_2$ and Fv fragments, can retain binding activity for a cognate receptor and, thus, are included within the definition of antibody. In addition, the term "antibody," as used herein, encompasses non-naturally occurring antibodies and fragments usually containing, at a minimum, one $V_H$ and one $V_L$ domain, such as chimeric antibodies, humanized antibodies and single chain Fv fragments (scFv) that specifically or selectively bind the appropriate cognate receptor. Such non-naturally occurring antibodies can be constructed using solid phase peptide synthesis, produced recombinantly or obtained by screening phage-displayed or other combinatorial libraries such as those consisting of variable heavy and light chains as described in Borrebaeck (Ed.), *Antibody Engineering* (Second edition) New York: Oxford University Press (1995)) using, for example, an assay described herein below.

Homing molecules which are antibodies also can be prepared using a cognate receptor fusion protein or a synthetic peptide encoding a portion of a cognate receptor. One skilled in the art understands that purified human or other cognate receptors, which can be produced recombinantly, including peptide portions of a cognate receptor such as synthetic peptide fragments can be used as immunogens. It is understood that fragments of the cognate receptor for SEQ ID NO: 6 useful as immunogens include fragments of the cognate receptor that serve to produce anti-cognate receptor antibodies which are readily internalized into cells expressing cell-surface cognate receptor for SEQ ID NO: 6. One skilled in the art further understands that non-immunogenic fragments or synthetic peptides of a cognate receptor for SEQ ID NO: 3, SEQ ID NO: 6 or SEQ ID NO: 7 can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988)).

A variety of therapeutic moieties are useful in the conjugates and methods of the invention, including, without limitation, anti-angiogenic agents and cytotoxic agents, such as those that target a DNA-associated process. As used herein, the term "therapeutic moiety" is used broadly to mean a physical, chemical, or biological material that can be linked to a homing molecule and that alters biological activity in a normal or pathologic tissue upon administration. A therapeutic moiety, therefore, is potentially useful for the treatment of disease conditions. A therapeutic moiety can be any natural or nonnatural material including a biological material, such as a cell or phage; an organic chemical, such as a small molecule; a radionuclide; a nucleic acid molecule or oligonucleotide; a polypeptide; or a peptide or peptidomimetic. Therapeutic moieties useful in the invention include, without limitation, anti-angiogenic agents; cancer chemotherapeutic agents; cytotoxic agents; pro-apoptotic agents. A therapeutic moiety useful in the invention can be expressed on, contained in, or linked to any of the following: phage or other virus, cell, liposome, polymeric or non-polymeric matrix, gold or other particle, or a microdevice, nanodevice, or nano-scale semiconductor material. These and other materials known in the art can be components of the conjugates of the invention.

A therapeutic moiety useful in a conjugate of the invention can be, for example, an anti-angiogenic agent. As used herein, the term "anti-angiogenic agent" means a molecule that reduces or inhibits angiogenesis. An anti-angiogenic agent useful in the conjugates and methods of the invention can be, for example, an inhibitor or neutralizing antibody that reduces the expression or signaling of an angiogenic factor such as vascular endothelial growth factor (VEGF), which is a major inducer of angiogenesis in normal and pathological conditions, and is essential in embryonic vasculogenesis. The biological effects of VEGF include stimulation of endothelial cell proliferation, survival, migration and tube formation, and regulation of vascular permeability. An anti-angiogenic agent also can inhibit another angiogenic factor such as a member of the fibroblast growth factor (FGF) family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)) or angiopoietin-1, a factor that signals through the endothelial cell-specific Tie2 receptor tyrosine kinase (Davis et al., *Cell* 87:1161-1169 (1996); and Suri et al., *Cell* 87:1171-1180 (1996)), or the receptor of one of these angiogenic factors. It is understood that a variety of mechanisms can act to inhibit activity of an angiogenic factor including, without limitation, direct inhibition of receptor binding or of secretion of the angiogenic factor into the extracellular space, and inhibition of signaling, expression or function of the angiogenic factor.

A variety of anti-angiogenic agents useful in the invention are known in the art and can be prepared by routine methods. See, for example, Hagedorn and Bikfalvi, *Crit. Rev. Oncol. Hematol.* 34:89-110 (2000) and Kirsch et al., *J. Neurooncol.* 50:149-163 (2000). Anti-angiogenic agents include, without limitation, small molecules; proteins such as angiogenic factors and receptors, transcription factors, and antibodies and antigen-binding fragments thereof; peptides and peptidomimetics; and nucleic acid molecules including ribozymes, antisense oligonucleotides, and nucleic acid molecules encoding, for example, dominant negative angiogenic factors and receptors, transcription factors, and antibodies and antigen-binding fragments thereof. Exemplary anti-angiogenic agents useful in the conjugates and methods of the invention include, yet are not limited to, angiostatin, endostatin, metastatin and 2ME2 (EntreMed; Rockville, Md.); anti-VEGF antibodies such as Avastin (Genentech; South San Francisco, Calif.); VEGFR-2 inhibitors such as the small molecules SU5416 and SU6668, (SUGEN; South San Francisco, Calif.); heparin-binding fragments of fibronectin; modified forms of antithrombin; collagenase inhibitors; basement membrane turnover inhibitors; angiostatic steroids; platelet factor 4, and fragments and peptides thereof; thrombospondin, and fragments and peptides thereof; and doxorubicin (O'Reilly et al., *Cell* 79:315-328 (1994)); O'Reilly et al., *Cell* 88: 277-285 (1997); Homandberg et al., *Am. J. Path.* 120:327-332 (1985); *Biochim. Biophys. Acta* 874:61-71 (1986); and O'Reilly et al., *Science* 285:1926-1928 (1999)). It is understood that these as well as other anti-angiogenic agents known in the art or that can be prepared by routine methods are encompassed by the term "anti-angiogenic agent" and can be used in the various conjugates and methods of the invention.

It is understood by those skilled in the art that an anti-angiogenic agent can be particularly efficacious when targeted to a specific stage of tumor progression (see, for example, Bergers et al., *Science* 284:808-812 (1999); and Bergers et al., *J. Clin. Invest.* 111:1287-1295 (2003)). Thus, in one embodiment, an anti-angiogenic agent useful in the invention is "effective against pre-malignant vasculature." As used herein, the term "anti-angiogenic agent effective against pre-malignant vasculature" means an angiogenic agent that can significantly reduce the number of angiogenic lesions during the pre-malignant phase of carcinogenesis, before solid tumors have formed. Such an anti-angiogenic agent is an anti-angiogenic agent effective against pre-malignant vasculature whether or not the agent also significantly reduces tumor burden or extends life-span in animals with tumors, including animals with small solid tumors or animals having large tumors and end-stage disease. As non-limiting examples, an anti-angiogenic agent effective against pre-malignant vasculature can be BB-94 (batimastat), a broad-spectrum inhibitor of matrix metalloproteinases (Talbot and Brown, *Eur. J. Cancer* 32A: 2528 (1996)); SU5416 (SUGEN), a small molecule inhibitor of VEGFR-2; or endostatin, a carboxy-terminal fragment of collagen XVIII (O'Reilly et al., *Cell* 88: 277 (1997); and Boehm et al., *Nature* 390: 404 (1997)), alone or combined with angiostatin, an internal fragment of plasminogen (O'Reilly et al., *Cell* 79: 314 (1994); and O'Reilly et al., *Nature Med.* 2: 689 (1996)). See, also, Bergers et al., supra, 1999; Bergers et al., supra, 2003.

An anti-angiogenic agent useful in the invention also can be an anti-angiogenic agent effective against tumor vasculature. As used herein, the term "anti-angiogenic agent effective against tumor vasculature" means an angiogenic agent that can significantly reduce tumor burden or extend life-span of animals having solid, vascularized tumors. Such an anti-angiogenic agent is an anti-angiogenic agent effective against tumor vasculature if there is efficacy against one or more of the following: small solid tumors, tumors with well-defined margins, invasive tumors or end-stage cancer, whether or not the agent significantly reduces the number of angiogenic lesions during the pre-malignant phase of carcinogenesis. As non-limiting examples, an anti-angiogenic agent effective against tumor vasculature can be efficacious only against small vascularized tumors, or against large tumors as well as small vascularized tumors. An anti-angiogenic agent effective against tumor vasculature can be, without limitation, an anti-angiogenic agent such as BB-94 (batimastat), endostatin, or angiostatin, which is effective against small tumors without significant efficacy on the large tumors characteristic of end-stage cancer (Bergers et al., supra, 1999). An anti-angiogenic agent effective against tumor vasculature further can be an anti-angiogenic agent effective against small tumors as well as large tumors in animals with short life expectancy such as, without limitation, AGM-1470 (TNP470), a small molecule inhibitor of endothelial cell proliferation (Ingber et al., *Nature* 348:555 (1990); Griffith et al., *Chem. Biol.* 4:461 (1997); Sin et al., *Proc. Natl. Acad. Sci. U.S.A.* 94:6099 (1997); and Castronovo and Belotti, *Eur. J. Cancer* 32A:2520 (1996)).

A therapeutic moiety useful in a conjugate of the invention further can be, for example, a therapeutic moiety with cytotoxicity against pericytes such as, without limitation, platelet-derived growth factor receptor-positive pericytes. Such a therapeutic moiety, for example, SU6668, can block further growth of end-stage tumors (Bergers et al., supra, 2003). Exemplary conjugates include, without limitation, conjugates containing a therapeutic moiety with cytotoxicity against pericytes linked to a homing peptide or peptidomimetic that selectively homes to vasculature of malignant skin and containing the amino acid sequence CGKRK (SEQ ID NO: 6) or the amino acid sequence CDTRL (SEQ ID NO: 7) or a conservative variant or peptidomimetic thereof.

A therapeutic moiety useful in a conjugate of the invention can be, for example, a cytotoxic agent. As used herein, the term "cytotoxic agent" means any molecule that results in cell death by any mechanism. Exemplary cytotoxic agents useful in a conjugate of the invention encompass, without limitation, taxanes such as docetaxel; anthracyclins such as doxorubicin; alkylating agents; vinca alkaloids; anti-metabolites; platinum agents such as cisplatin or carboplatin; steroids such as methotrexate; antibiotics such as adriamycin; antimicrobial peptides, described herein below; and other cancer chemotherapeutic agents, which are chemical agents that inhibit the proliferation, growth, life-span or metastatic activity of cancer cells.

Effective cytotoxic agents useful in the invention include those that target DNA, for example, alkylating agents, agents that intercalate into DNA, and agents which result in double-stranded DNA breaks. Exemplary DNA-targeted drugs include, without limitation, cyclophosphamide, melphalan, mitomycin C, bizelesin, cisplatin, doxorubicin, etoposide, mitoxantrone, SN-38, Et-743, actinomycin D, bleomycin, TLK286 and SGN-15 (Hurley, supra, 2002). It is understood that DNA-targeting cytotoxic agents can be particular useful when combined in conjugates with a homing molecule that localizes, at least in part, to the nuclei of cells. Thus, in one embodiment the invention provides a conjugate containing a therapeutic moiety linked to a homing peptide or peptidomimetic that selectively homes to vasculature of malignant skin and which specifically binds a cognate receptor for SEQ ID NO: 6, where the therapeutic moiety is a cytotoxic agent that targets a DNA-associated process. In a further embodiment, the invention provides a conjugate containing a therapeutic moiety linked to a homing peptide or peptidomimetic which selectively homes to vasculature of malignant skin and which includes the amino acid sequence SEQ ID NO: 6 or a conservative variant or peptidomimetic thereof. Useful cytotoxic agents that target a DNA-associated process include, without limitation, alkylating agents, anti-tumor antibiotics and sequence-selective agents and further encompass agents such as cyclophosphamide, melphalan, mitomycin C, bizelesin, cisplatin, doxorubicin, etoposide, mitoxantrone, SN-38, Et-743, actinomycin D, bleomycin and TLK286.

Taxanes are cytotoxic agents useful in a conjugate of the invention. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., *J. Clin. Oncol.* 17:2341-2354 (1999), and Paridaens et al., *J. Clin. Oncol.* 18:724 (2000).

A cytotoxic agent useful in a conjugate of the invention also can be an anthracyclin such as doxorubicin, idarubicin or daunorubicin. Doxorubicin is a commonly used cancer chemotherapeutic agent (Stewart and Ratain, In: "Cancer: Principles and practice of oncology" 5th ed., chap. 19 (eds. DeVita, Jr., et al.; J.P. Lippincott 1997); Harris et al., In "Cancer: Principles and practice of oncology," supra, 1997). In addition, doxorubicin has anti-angiogenic activity which can contribute to its effectiveness in treating cancer (Folkman, supra, 1997; Steiner, In "Angiogenesis: Key principles-Science, technology and medicine," pp. 449-454 (eds. Steiner et al.; Birkhauser Verlag, 1992)).

An alkylating agent such as melphalan or chlorambucil also can be a cytotoxic agent useful in a conjugate of the invention. Similarly, a vinca alkaloid such as vindesine, vinblastine or vinorelbine; or an antimetabolite such as 5-fluorouracil, 5-fluorouridine or a derivative thereof can be a cytotoxic agent that can be linked to a homing molecule in a conjugate of the invention.

Cytotoxic agents useful in the conjugates of the invention also include, without limitation, platinum agents. Such a platinum agent can be, for example, cisplatin or carboplatin as described, for example, in Crown, *Seminars in Oncol.* 28:28-37 (2001). Other cytotoxic agents useful in a conjugate of the invention include, but are not limited to, methotrexate, mitomycin-C, adriamycin, ifosfamide and ansamycins.

A cytotoxic agent also can be, for example, an antimicrobial peptide. In one embodiment, the invention provides a conjugate in which a homing molecule that selectively homes to vasculature of pre-malignant dysplastic skin and that specifically binds a cognate receptor for SEQ ID NO: 3 is linked to an antimicrobial peptide, where the conjugate is selectively internalized by vasculature of a pre-malignant dysplastic lesion, and where the antimicrobial peptide has low mammalian cell toxicity when not linked to the homing molecule. In another embodiment, the invention provides a conjugate in which a homing molecule that selectively homes to vasculature of malignant skin and that specifically binds a cognate receptor for SEQ ID NO: 6 or SEQ ID NO: 7 is linked to an antimicrobial peptide, where the conjugate is selectively internalized by vasculature of malignant skin, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide can kill or slow the growth of, for example, one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., *J. Med. Chem.* 39:3107-3113 (1996); and Blondelle and Houghten, *Biochem.* 31: 12688-12694 (1992). An antimicrobial peptide also can be, for example, a β-strand/sheet-forming peptide as described in Mancheno et al., *J. Peptide Res.* 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274: 151-155 (1990); and Blondelle and Houghten in Bristol (Ed.), *Annual Reports in Medicinal Chemistry* pages 159-168 Academic Press, San Diego)). As discussed further below, an antimicrobial peptide also can be an analog of a natural peptide, especially one that retains or enhances amphipathicity.

An antimicrobial peptide incorporated within a conjugate of the invention has low mammalian cell toxicity when not linked to a homing molecule of the invention. Mammalian cell toxicity readily can be assessed using routine assays. For example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM for lytic activity.

In one embodiment, the invention provides a conjugate in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, for example, is an antimicrobial peptide which induces marked mitochondrial swelling at a concentration of 10 μM, significantly less than the concentration required to kill eukaryotic cells. An antimicrobial peptide that induces significant mitochondrial swelling at, for example, 50 μM, 40 μM, 30 μM, 20 μM, 10 μM, or less, is considered a peptide that promotes disruption of mitochondrial membranes.

An antimicrobial peptide portion can include, for example, the sequence (KLAKLAK)$_2$ (SEQ ID NO: 13), (KLAKKLA)$_2$ (SEQ ID NO: 14), (KAAKKAA)$_2$ (SEQ ID NO: 15), or (KLGKKLG)$_3$ (SEQ ID NO: 16), and, in one embodiment, includes the sequence $_D$(KLAKLAK)$_2$. A conjugate of the invention, which contains a homing molecule that selectively homes to vasculature of pre-malignant dysplastic skin linked to an antimicrobial peptide, can include, for example, the sequence SRPRR-GG-$_D$(KLAKLAK)$_2$ or the sequence CSRPPRSEC-GG-$_D$(KLAKLAK)$_2$. Similarly, a conjugate of the invention containing a homing molecule that selectively homes to vasculature of malignant skin linked to an antimicrobial peptide, can include, for example, the sequence CGKRK-GG-$_D$(KLAKLAK)$_2$ or the sequence CDTRL-GG-$_D$(KLAKLAK)$_2$.

Antimicrobial peptides generally have random coil conformations in dilute aqueous solutions, yet can be induced to high levels of helicity with helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, *Proteins: Structures and Molecular Properties* W.H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., *Biochim. Biophys. Acta* 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., *Biopolymers* 37:105-122 (1995)). Synthetic antimicrobial peptides having an amphipathic α-helical structure are known in the art as described, for example, in U.S. Pat. No. 5,789,542 to McLaughlin and Becker.

It is understood by one skilled in the art of medicinal oncology that these and other agents are useful therapeutic moieties, which can be used separately or together in the conjugates and methods of the invention. It further is understood that a conjugate of the invention can contain one or more of such therapeutic moieties and that additional components can be included as part of the conjugate, if desired. As an example, in some cases it can be desirable to utilize an oligopeptide spacer between the homing molecule and the therapeutic agent (Fitzpatrick and Garnett, *Anticancer Drug Des.* 10:1-9 (1995)).

In further embodiments, a conjugate of the invention includes a detectable moiety. As used herein, the term "detectable moiety" means any molecule which can be administered in vivo and subsequently detected. Exemplary detectable moieties useful in the conjugates and methods of the invention include, without limitation, radiolabels and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red.

The methods of the invention for imaging the vasculature of a pre-malignant dysplastic tissue such as dysplastic skin or the vasculature of a malignant tissue can be useful for early detection of dysplastic lesions or malignancies including but not limited to, dermatological dysplasias and malignancies. Following administration of a conjugate of the invention containing a detectable moiety, the vasculature of pre-malignant dysplastic tissue or malignant tissue is visualized. If the image is positive for the presence of such vasculature, further evaluation can be performed for the size of the tumor, if any, and the quantity of vascular infiltration. These results provide valuable information to the clinician with regard to the stage of development of the cancer and the presence or probability of metastasis.

It is understood that the methods of the invention are applicable to a variety of types of pre-malignancies and malignancies including, yet not limited to, squamous cell dysplasias and carcinomas, melanomas and other dermatological dysplasias and malignancies; breast dysplasias and malignancies; ovarian dysplasias and malignancies; cervical dysplasias and malignancies; prostate dysplasias and malignancies; lung dysplasias and malignancies; and other epitheliomas, epithelial cell dysplasias and malignancies.

The methods of the invention are applicable to a variety of neoplasms of epithelial origin ranging from benign to malignant and including dermatological and non-dermatological dysplasias and malignancies. As non-limiting examples, the methods of the invention are applicable to a variety of types of dermatological dysplasias and malignancies such as squamous cell carcinomas, basosquamous cell carcinomas, basal cell carcinomas, cancer en cuirasse and Merkel cell carcinomas. As further non-limiting examples, the methods of the invention are applicable to, without limitation, breast carcinomas including apocrine cell carcinomas; acinar cell carcinomas such as of the breast or salivary gland; ductal carcinomas such as those of the pancreas or breast; endometrial carcinomas; alveolar and bronchiogenic carcinomas including adenocarcinomas of the lung, large cell carcinomas, small cell carcinomas (small cell lung cancers) and squamous cell carcinomas; giant cell carcinomas, for example, of the lung or thyroid gland; gastric carcinomas such as adenocarcinomas and carcinoid tumors of the small or large intestine; schistosomal bladder carcinomas; intra- and extrahepatic bile duct carcinomas; hepatocellular carcinomas (hepatomas, hepatocarcinomas); renal cell carcinomas; thyroid gland carcinomas; epithelial tumors of the salivary gland; adenocystic and adenoid squamous cell carcinomas, adenomas; nasopharyngeal carcinomas; meningeal carcinomas; and embryonal carcinomas. One skilled in the art understands that the methods of the invention, including but not limited to methods of directing a moiety to vasculature of a malignant tissue, can be applied to any of the above and other epithelial dysplasias and malignancies. In particular embodiments, the methods of the invention rely on a conjugate containing a moiety linked to a homing molecule that selectively homes to vasculature of malignant skin and which specifically binds a cognate receptor for SEQ ID NO: 6 or SEQ ID NO: 7 in order to direct a moiety, image vasculature or treat one of the above-specified dysplasias or malignancies.

In a method of the invention for imaging vasculature of a pre-malignant dysplastic tissue, the conjugate administered contains a detectable moiety that allows detection or visualization of the vasculature of the pre-malignant dysplastic tissue such as dysplastic skin. In a method of the invention for imaging vasculature of a malignant tissue, the conjugate administered contains a detectable moiety that allows detection or visualization of the vasculature of the malignant tissue such as malignant skin. For such in vivo diagnostic imaging, a homing molecule is linked to a detectable moiety that, upon administration to the subject, is detectable external to the subject. Such a detectable moiety can be, for example, a gamma ray emitting radionuclide such as indium-113, indium-115 or technetium-99; following administration to a subject, the conjugate can be visualized using a solid scintillation detector.

It is understood that a variety of routes of administration are useful in the methods of the invention. Such routes encompass systemic and local administration and include, without limitation, oral administration, topical application, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants.

As disclosed herein, several homing peptides identified as selectively homing to vasculature of pre-malignant dysplastic skin such as homing peptides SEQ ID NOS: 3, 4 and 5 share the sequence SRPRR (SEQ ID NO: 1), present in kallikrein 9. Thus, a cognate receptor for a homing molecule that selectively homes to vasculature of pre-malignant dysplastic skin can be a molecule that specifically binds a kallikrein 9 binding molecule such as a kallikrein 9 substrate or inhibitor. Based on the results disclosed herein, the present invention provides a method of isolating one or more homing molecules that selectively home to vasculature of pre-malignant dysplastic skin by contacting a kallikrein 9 binding molecule, or a fragment thereof, with a library of molecules under conditions suitable for specific binding of a molecule to the kallikrein 9 binding molecule; assaying for specific binding; and separating from the library one or more molecules that specifically bind the kallikrein 9-binding molecule, thereby isolating one or more homing molecules that selectively home to vasculature of pre-malignant dysplastic skin.

As non-limiting examples, native, recombinant and human kallikrein 9-binding molecules, and fragments of a kallikrein 9-binding molecule including fragments that bind SEQ ID NOS: 3, 4 or 5, whether purified or expressed on the surface of a cell, can be useful in the screening methods of the invention. In one embodiment, the kallikrein 9-binding molecule is a kallikrein 9 inhibitor. In another embodiment, the kallikrein 9-binding molecule is an isolated kallikrein 9 binding molecule. In a further embodiment, the kallikrein 9-binding molecule is cell-surface expressed molecule. It is understood that libraries that can be screened according to a method of the invention include, but are not limited to, libraries of peptides and peptidomimetics, libraries of small molecules, and libraries of antibodies and antigen-binding fragments thereof, including synthetic, single-chain or other antibody libraries.

The following examples are intended to illustrate but not limit the present invention.

Example I

Phage that Selectively Home to Dysplastic Skin

This example describes identification of a peptide that selectively homes to dysplastic skin lesions.

To isolate peptides specific for dysplastic lesions, two rounds of selection were performed ex vivo followed by one round of selection in vivo. Ex vivo and in vivo phage selections were performed with an NNK-encoded $CX_7C$ (SEQ ID NO: 8) peptide library displaying 9-mer cyclic peptides with seven degenerate positions on Novagen's T7 415-1b phage vector; the library had a diversity of approximately $1 \times 10^8$. Phage selections and validations were performed essentially as described in Laakkonen et al., Nat. Med. 8:751-755 (2002).

For ex vivo selections, phage were incubated with dispersed cells from dysplastic skin removed from the ears and chest of K14-HPV16 mice with no macroscopic evidence of tumors at 4-6 months of age. The dysplastic skin lesions typically included a focal region of epidermal dysplasia flanked by adjacent hyperplastic epidermis, along with underlying reactive stromal elements and angiogenic endothelium in the aberrant dermis. A portion of each dysplastic skin tissue biopsy used for ex vivo or in vivo phage selection was fixed in formalin and, after conventional processing, examined histologically to assess the neoplastic grade. Hematoxylin and eosin stained paraffin sections confirmed that the areas of skin used in the selection steps were largely made up of focal dysplasias.

Sequential ex vivo selections on cell suspensions of dysplastic skin resulted in a 160-fold enrichment of phage relative to similar treatment with non-recombinant phage lacking displayed peptides (FIG. 1A, left); greater than 10,000-fold enrichment resulted from the subsequent round of in vivo selection (see FIG. 1A, right). Selection in vivo also produced a minor enrichment of phage that homed to control brain, kidney and hyperplastic skin tissues. DNA sequence analysis of 48 clones isolated in the second ex vivo round and 48 clones from the subsequent in vivo round characterized the sequences of the $CX_7C$ (SEQ ID NO: 8) homing peptides. Of the 96 phage clones analyzed, nine peptides appeared most frequently and were further analyzed as described below.

To test homing specificity of the selected peptides, purified phage displaying a single recombinant sequence were intravenously injected into K14HPV16 mice bearing protuberant ear or trunk tumors at 9 to 12 months of age to assess homing to squamous cell carcinomas, or alternatively injected into younger K14HPV16 mice presenting with multifocal dysplasias but no tumors. Both neoplastic tissues and normal control organs were collected and assayed for phage accumulation. Phage displaying the peptide CRAKSKVAC (SEQ ID NO: 9), which appeared with the highest frequency in both the ex vivo and in vivo sequence pools (5 and 15 times, respectively), were 1500-fold enriched in dysplastic skin relative to non-recombinant control phage. However, phage displaying peptide. SEQ ID NO: 9 accumulated with similar frequency in normal skin, kidney and brain, indicating that the CRAKSKVAC (SEQ ID NO: 9) peptide homes to an abundant signal in each of these organs and is not specific to dysplastic skin lesions. Several other dysplasia-selected clones also differentiated poorly between control tissues and dysplastic skin; seven of the nine dysplasia-selected phage clones appeared to be responsible for the overall enrichment of recombinant phage in control tissues in the final in vivo round of selection as shown in FIG. 1A (right panel), and were not studied further.

Peptides displayed on the two remaining phage clones were found to be highly selective for dysplastic skin, and did not appreciably home to normal organs. One of these peptides, CNRRTKAGC (SEQ ID NO: 10), is closely related to a previously described peptide that homes to tumor lymphatic vessels (Laakkonen, supra, 2002). The second dysplasia-homing peptide, CSRPRRSEC (SEQ ID NO: 3), appeared three times amongst the 48 phage sequenced from the in vivo round, along with two variants, CSRPRRSVC (SEQ ID NO: 4) and CSRPRRSWC (SEQ ID NO: 5), that each appeared once. Phage displaying the CSRPRRSEC (SEQ ID NO: 3) peptide were enriched ~350-fold in dysplastic skin and did not significantly accumulate in control tissues (FIG. 1C, left panel). Furthermore, when injected into a K14HPV16 mouse bearing an ear tumor as well as multifocal skin dysplasias, CSRPRRSEC (SEQ ID NO: 3)-displaying phage effectively homed to dysplastic chest skin and dysplastic ear skin, but showed little homing to the tumor (FIG. 1C, right panel). In addition, CSRPRRSEC (SEQ ID NO: 3)-bearing phage did not home to normal skin of FVB/n mice in vivo and further did not bind to hyperplastic skin of 1 to 2 month-old K14-HPV16 mice in ex vivo experiments (FIG. 1C, left and right panels).

These results demonstrate that the CSRPRRSEC (SEQ ID NO: 3) peptide selectively homes to dysplastic skin lesions and further indicate that this peptide binds to a receptor which is present in pre-malignant skin dysplasias but which is essentially absent or inaccessible via the circulation in normal skin and in skin malignancies such as squamous cell carcinomas. Given that peptide CSRPRRSEC (SEQ ID NO: 3) localizes to endothelial cells, these results further indicate that homing selectivity is attributable to vascular changes during the carcinogenic progression from normal skin to dysplasia and then to cancer.

Example II

Tumor-Specific Homing Phage

This example describes identification of phage that selectively home to malignant skin such as squamous cell carcinomas.

To isolate phage that selectively home to squamous cell carcinomas (SCCs), two rounds of ex vivo panning selections were performed followed by two rounds of in vivo panning in K14-HPV16 mice having tumors histologically confirmed as squamous cell carcinoma grades II-IV (Coussens, supra, 1996). The enrichment rose from 6-fold relative to non-recombinant phage in the second ex vivo round to greater than 70-fold relative to non-recombinant phage in the second in vivo round (the fourth sequential round overall) as shown in FIG. 1B. From 192 sequenced phage clones, fifteen were selected for further analysis based on their frequency (48 from ex vivo round 2, 48 from in vivo round 1, and 96 from in vivo round 2) and their increased prevalence in the in vivo selections. Of these, four clones displaying the following amino acid sequences bound to a K14-HPV16 tumor-derived cell suspension ex vivo: CGKRK (SEQ ID NO: 6), CGTKRKC (SEQ ID NO: 11), CDTAVVEGL (SEQ ID NO: 12) and CDTRL (SEQ ID NO: 7). Phage-displaying the sequence CDTAVVEGL (SEQ ID NO: 12) also were 340-fold enriched in tumors in vivo relative to non-recombinant control phage.

When intravenously injected into tumor-bearing K14-HPV16 mice, CGKRK (SEQ ID NO: 6) phage showed a marked preference for the tumor, with an efficiency that varied from 80 to 1,000-fold in independent experiments. Some homing to dysplastic lesions was observed in the one of two experiments that showed an 80× enrichment in the tumor (FIG. 1D). Normal and, hyperplastic skin, and various control organs, accumulated very low levels of the CGKRK (SEQ ID NO: 6) phage. Similar analysis of the CDTRL (SEQ ID NO: 7) phage revealed a variable preference for squamous cell carcinomas and dysplastic lesions; in one experiment the phage accumulated more effectively in dysplastic lesions than in a tumor, whereas the reverse was true in another experiment (FIG. 1E). This phage showed little affinity for hyperplastic skin, and no significant homing to normal skin from FVB/n mice (FIG. 1E). Thus, phage displaying peptide CDTRL (SEQ ID NO: 7) were variably selective for both dysplasias and squamous tumors of the epidermis, indicative of lesional heterogeneity in the CDTRL (SEQ ID NO: 7) receptor.

Example III

Intra-Tissue Localization of Homing Peptides

This example describes localization of several homing peptides.

To characterize the nature of the selectivity of the dysplasia- and tumor-homing peptides, K14-HPV16 mice were intravenously injected with cloned phage displaying a particular peptide, and phage localization visualized using histological procedures. Peptide localization was further analyzed with chemically synthesized fluorescein-labeled peptides.

Phage were intravenously injected into 4 to 6 month-old dysplasia-bearing mice with dysplasia-homing phage bearing CSRPRRSEC (SEQ ID NO: 3). In parallel, a set of 9 to 12 month-old tumor-bearing mice were infused with one of the tumor-homing phage CGTKRKC (SEQ ID NO: 11), CGKRK (SEQ ID NO: 6) or CDTRL (SEQ ID NO: 7). Various tissues were collected from each mouse and analyzed by double label immunohistochemical staining using an anti-T7 antibody to detect phage and an anti-CD31 antibody to detect endothelial cells of the vasculature. As shown in FIG. 2, phage co-localized in each case with CD31-positive endothelial cells in the expected target tissue. In particular, CSRPRRSEC (SEQ ID NO: 3)-phage accumulated in dysplastic skin (FIG. 2A) of dysplastic mice, CGTKRKC (SEQ ID NO: 11) phage were also detected to a lesser extent in dysplastic skin of tumor-bearing mice (FIG. 2B), CGKRK (SEQ ID NO: 6) phage accumulated in tumor tissue (FIG. 2C), and CDTRL (SEQ ID NO: 7) phage were localized to large, dilated vessels throughout the dysplastic and hyperplastic skin (FIG. 2D) as well as in tumors (FIG. 2E).

To further evaluate homing selectivity of displayed peptides, synthetic peptides were analyzed outside of the context of phage particles. Both younger dysplasia-bearing and older tumor-bearing K14-HPV16 mice were injected with fluorescein-labeled peptides. After 10 minutes, both normal and neoplastic tissues were collected; tissue sections were prepared and stained with antibodies to both CD31 and a second endothelial marker, the cell-surface antigen Meca-32. Similar results were obtained with the two endothelial marker antibodies; the data for Meca-32 are shown in FIG. 3, in which localization of intravenously infused peptides and antibody was visualized by two-color fluorescence microscopy.

As shown in FIG. 3, fluorescein-labeled peptides co-localized with Meca-32 in target neoplastic tissue after intravenous injection, and were not detected in tissues where the corresponding phage, did not home. Specifically, fluorescein-labeled CSRPRRSEC (SEQ ID NO: 3) co-localized with Meca-32 in dysplastic skin vasculature from both non-tumor-bearing (FIG. 3A) and tumor-bearing mice (FIG. 3D, inset); notably, the peptide was not detected within the squamous tumor in the latter (FIG. 3D), confirming its selectivity for premalignant dysplastic vasculature. In contrast, fluorescein-labeled CGKRK (SEQ ID NO: 6) and CDTRL (SEQ ID NO: 7) peptides were not detected in the dysplastic skin of younger non-tumor bearing mice (FIGS. 3B and 3C) but were primarily detected in tumor vasculature (FIGS. 3E and F), and at lower levels in the dysplastic skin of these tumor-bearing mice. Together with the immunolocalization analyses of phage homing, the peptide localization data indicate that CGKRK (SEQ ID NO: 6) and CDTRL (SEQ ID NO: 7) home specifically to blood vessels in squamous cell carcinomas and in the dysplastic foci of tumor-bearing mice, but not to vasculature of earlier stage dysplasias in non-tumor bearing mice.

Areas of skin, tumors and various organs were collected and either fixed in formalin, dehydrated through serial alcohols and embedded in paraffin, or directly embedded in OCT medium (Fisher Scientific). K14-HPV16 dysplasia and tumor samples were graded by evaluating hematoxylin & eosin and anti-keratin staining on 5 μm paraffin sections under a light microscope (Coussens et al., supra, 1996). Rat anti-mouse CD31 and rat anti-mouse Meca-32 (BD Pharmingen; San Diego, Calif.) were used for vascular immunostaining on 10 μm frozen sections. Anti-phage staining and biodistribution of fluorescein-labeled peptides were performed essentially as described in Laakkonen et al., supra, 2002.

Example IV

Tumor-Type Specificity of Peptide Homing

This example describes tumor-type specificity of peptide homing.

Peptides identified by their binding to endothelial cells in skin dysplasias or skin tumors could in principle be selective for neoplasias in this tissue, neoplasias of this cell type, neoplasias induced by these oncogenes, or be general to neoplasias in various tissues and of various cell types and oncogenic transformations.

To analyze homing selectivity, the K14-HPV16 squamous cell cancer-homing peptides, CGKRK (SEQ ID NO: 6) and CDTRL (SEQ ID NO: 7), were analyzed for the ability to home to endothelium in tumors of different tissue origins and in tumors localized to different anatomical locations. In particular, three subcutaneously implanted tumors and two tumors produced in transgenic animal models were examined for accumulation of fluorescein-labeled peptides following intravenous injection As shown in FIG. 4, different homing specificities were observed for each peptide in the various tumor microenvironments. In particular, in FIGS. 4A and F, neither peptide CGKRK (SEQ ID NO: 6) nor CDTRL (SEQ ID NO: 7) homed to angiogenic islets (dysplasias) or tumors in the RIP-Tag transgenic mouse model of pancreatic islet cell carcinoma (Hanahan, *Nature* 315:115-122 (1985)), indicating that the binding moieties for these peptides are not present in normal, dysplastic, or pancreatic tumor vasculature. However, both CGKRK (SEQ ID NO: 6) and CDTRL (SEQ ID NO: 7) did home to breast carcinomas in the MMTV-PyMT transgenic mouse model (Guy et al., *Mol. Cell. Biol.* 12:954-961 (1992)) as shown in FIGS. 4B and G. Some of the positive cells appeared to be circulation-accessible tumor cells (Chang et al., *Proc. Natl. Acad. Sci. USA* 97:14608-14613 (2000)), indicating that the CGKRK (SEQ ID NO: 6) and CDTRL (SEQ ID NO: 7) peptide binding receptors can have broader representation beyond tumor endothelial cells (see FIG. 4G). Both CGKRK (SEQ ID NO: 6) and CDTRL (SEQ ID NO: 7) bind a range of cultured tumor cells in addition to homing to tumor endothelial cells in vivo. Further, the activated endothelium in the MMTV-PyMT mouse breast tumor model shares molecular determinants with squamous cell carcinomas of the skin as detected by these peptides; these determinants are not present in the RIP-Tag model of endocrine pancreatic cancer. Skin squamous cell carcinoma tumorigenesis is induced by the E6 and E7 oncogenes of HPV16, while both RIP-Tag and MMTV-PyMT tumors are induced by the polyoma middle T-antigen, indicating that homing selectivity is not dependent on transformation by a particular oncogene or oncogenes.

The two tumor peptides showed different homing specificity when assayed for the ability to home to three types of subcutaneously grown transplanted tumors. Fluorescein-CGKRK (SEQ ID NO: 6) peptide homed to cells in each of the three transplant tumors (FIGS. 4C-E), which arose from PDSC5, a K14-HPV16 tumor-derived cell line (FIG. 4C); the MDA-MB-435 human breast cancer line (FIG. 4D; Price et al., *Cancer Res.* 50:717-721 (1990)); or the C8161 human melanoma line (FIG. 4E; Bregman and Meyskens, *Int. J. Cancer* 37:101-107 (1986)). In contrast, the CDTRL (SEQ ID NO: 7) peptide accumulated only in the melanoma xenografts (FIG. 4J) and in the skin overlying the melanoma xenograft tumor (FIG. 4J inset). Furthermore, fluorescein-CGKRK (SEQ ID NO: 6) localized in the cytoplasm and nuclei of vascular cells identified as endothelial cells by their morphology and by immunostaining for CD31 and Meca-32 (see FIG. 4D). In addition, peptide CGKRK (SEQ ID NO: 6) apparently extravasated out of the vessels and distributed along tendril-like structures and in tumor cell nuclei; the peptide also accumulated to some extent in avascular necrotic regions (FIGS. 4B, C and E). Given that all three tumors were growing subcutaneously, by presumably recruiting neovasculature from the same normal vascular bed, these results indicate that cell type or oncogenic stimulus imparts different qualities onto vasculature and the tumor microenvironment, as revealed by differential selective homing patterns seen with these peptides.

RIP1-Tag2 mice were used at 12 weeks of age, at which time all mice had pancreatic islet tumors. MMTV-PyMT mice were 4 to 6 months old and carried palpable mammary tumors. Cells for subcutaneous inoculation to produce transplant tumors were cultured in 10% fetal calf serum (FCS) in Dulbecco's Modified Eagle's Media (DMEM). Tumors were generated by subcutaneously injecting $10^6$ cells into the chest skin of FVB/n (PDSC5) or Balb/c nude (MDA-MB-435 and C8161) mice. Mice bearing subcutaneous transplant tumors had tumors with an approximate diameter of 1 centimeter. PDSC5 tumors and MDA-MB-435 xenografts reached this size about 9 weeks post-injection while C8161 xenografts reached a size of 1 cm about three weeks post-injection.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

What is claimed is:

1. A conjugate, comprising a moiety linked to a homing peptide that selectively homes to vasculature of pre-malignant dysplastic skin, wherein said homing peptide comprises the amino acid sequence CXSRPRRZC (SEQ ID NO: 2)
   wherein X=0 to 20 independently selected residues and
   wherein Z=0 to 20 independently selected residues.

2. An isolated peptide, having a length of less than 45 residues and comprising the amino acid sequence CXSRPRRZC (SEQ ID NO: 2),
   wherein X=0 to 20 independently selected residues and
   wherein Z=0 to 20 independently selected residues.

3. The isolated peptide of claim 2, which is conformationally constrained.

4. The isolated peptide of claim 3, which is cyclic.

5. The conjugate of claim 1, wherein said moiety is a therapeutic moiety.

6. The conjugate of claim 5, wherein said therapeutic moiety is an antiangiogenic agent.

7. The conjugate of claim 5, wherein said therapeutic moiety is a cytotoxic agent.

8. The conjugate of claim 1, wherein said moiety is a detectable moiety.

9. The conjugate of claim 8, wherein said detectable moiety is a radionuclide.

10. The conjugate of claim 8, wherein said detectable moiety is a fluorescent label.

11. The conjugate of claim 1, wherein the peptide comprises the amino acid sequence CSRPRRSEC (SEQ ID NO: 3).

12. The conjugate of claim 1, wherein the peptide comprises the amino acid sequence CSRPRRSVC (SEQ ID NO: 4).

13. The conjugate of claim 1, wherein the peptide comprises the amino acid sequence CSRPRRSWC (SEQ ID NO: 5).

14. The isolated peptide of claim 2, wherein the peptide has a length of less than 40 residues.

15. The isolated peptide of claim 2, wherein the peptide has a length of less than 35 residues.

16. The isolated peptide of claim 2, wherein the peptide has a length of less than 30 residues.

17. The isolated peptide of claim 2, wherein the peptide has a length of less than 25 residues.

18. The isolated peptide of claim 2, wherein the peptide has a length of less than 20 residues.

19. The isolated peptide of claim 2, wherein the peptide has a length of less than 15 residues.

20. The isolated peptide of claim 2, wherein the peptide has a length of less than 12 residues.

21. The isolated peptide of claim 2, wherein the peptide has a length of less than 10 residues.

22. The isolated peptide of claim 2, wherein the peptide has a length of less than 9 residues.

23. The isolated peptide of claim 2, wherein the peptide comprises the amino acid sequence CSRPRRSEC (SEQ ID NO: 3).

24. The isolated peptide of claim 2, wherein the peptide comprises the amino acid sequence CSRPRRSVC (SEQ ID NO: 4).

25. The isolated peptide of claim 2, wherein the peptide comprises the amino acid sequence CSRPRRSWC (SEQ ID NO: 5).

26. An isolated cyclic peptide having a length of less than 90 residues and comprising the amino acid sequence CXSRPRRZC (SEQ ID NO: 2),
    wherein X=0 to 20 independently selected residues and wherein Z=0 to 20 independently selected residues.

27. The isolated peptide of claim 26, wherein the peptide has a length of less than 80 residues.

28. The isolated peptide of claim 26, wherein the peptide has a length of less than 70 residues.

29. The isolated peptide of claim 26, wherein the peptide has a length of less than 60 residues.

30. The isolated peptide of claim 26, wherein the peptide has a length of less than 50 residues.

31. The isolated peptide of claim 26, wherein the peptide has a length of less than 45 residues.

32. The isolated peptide of claim 26, wherein the peptide has a length of less than 40 residues.

33. The isolated peptide of claim 26, wherein the peptide has a length of less than 35 residues.

34. The isolated peptide of claim 26, wherein the peptide has a length of less than 30 residues.

35. The isolated peptide of claim 26, wherein the peptide has a length of less than 25 residues.

36. The isolated peptide of claim 26, wherein the peptide has a length of less than 20 residues.

37. The isolated peptide of claim 26, wherein the peptide has a length of less than 15 residues.

38. The isolated peptide of claim 26, wherein the peptide has a length of less than 12 residues.

39. The isolated peptide of claim 26, wherein the peptide has a length of less than 10 residues.

40. The isolated peptide of claim 26, wherein the peptide has a length of less than 9 residues.

41. The isolated peptide of claim 26, wherein the peptide comprises the amino acid sequence CSRPRRSEC (SEQ ID NO: 3).

42. The isolated peptide of claim 26, wherein the peptide comprises the amino acid sequence CSRPRRSVC (SEQ ID NO: 4).

43. The isolated peptide of claim 26, wherein the peptide comprises the amino acid sequence CSRPRRSWC (SEQ ID NO: 5).

* * * * *

SEQUENCE LISTING

<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Ser Arg Pro Arg Arg
1               5

<210> SEQ ID NO 2
<211> LENGTH: 47
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)...(21)
<223> OTHER INFORMATION: Xaa = independently selected residue  that may
      or may not be present.
<220> FEATURE:
<221> NAME/KEY: VARIANT
<222> LOCATION: (27)...(46)
<223> OTHER INFORMATION: Xaa = independently selected residue  that may
      or may not be present.

<400> SEQUENCE: 2

Cys Xaa Xaa Xaa Xaa Xaa Xaa Xaa Xaa Xaa Xaa Xaa Xaa Xaa Xaa Xaa

```
                1               5                   10                  15
Xaa Xaa Xaa Xaa Xaa Ser Arg Pro Arg Arg Xaa Xaa Xaa Xaa Xaa Xaa
                    20                  25                  30

Xaa Xaa Xaa Xaa Xaa Xaa Xaa Xaa Xaa Xaa Xaa Xaa Xaa Cys
        35                  40                  45

<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Cys Ser Arg Pro Arg Arg Ser Glu Cys
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic construct

<400> SEQUENCE: 4

Cys Ser Arg Pro Arg Arg Ser Val Cys
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

Cys Ser Arg Pro Arg Arg Ser Trp Cys
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct

<400> SEQUENCE: 6

Cys Gly Lys Arg Lys
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic construct

<400> SEQUENCE: 7

Cys Asp Thr Arg Leu
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic construct
```

```
<220> FEATURE:
<221> NAME/KEY: VARIANT
<222> LOCATION: (2)...(8)
<223> OTHER INFORMATION: Xaa = any amino acid

<400> SEQUENCE: 8

Cys Xaa Xaa Xaa Xaa Xaa Xaa Cys
  1               5

<210> SEQ ID NO 9
<211> LENGTH: 9
<212> TYPE: PRT
<213> ORGANISM: Artificial Sequence
<220> FEATURE:
<223> OTHER INFORMATION: synthetic construct

<400> SEQUENCE: 9

Cys Arg Ala Lys Ser Lys Val Ala Cys
  1               5

<210> SEQ ID NO 10
<211> LENGTH: 9
<212> TYPE: PRT
<213> ORGANISM: Artificial Sequence
<220> FEATURE:
<223> OTHER INFORMATION: synthetic construct

<400> SEQUENCE: 10

Cys Asn Arg Arg Thr Lys Ala Gly Cys
  1               5

<210> SEQ ID NO 11
<211> LENGTH: 7
<212> TYPE: PRT
<213> ORGANISM: Artificial Sequence
<220> FEATURE:
<223> OTHER INFORMATION: synthetic construct

<400> SEQUENCE: 11

Cys Gly Thr Lys Arg Lys Cys
  1               5

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12

Cys Asp Thr Ala Val Val Glu Gly Leu
  1               5

<210> SEQ ID NO 13
<211> LENGTH: 14
<212> TYPE: PRT
<213> ORGANISM: Artificial Sequence
<220> FEATURE:
<223> OTHER INFORMATION: synthetic construct

<400> SEQUENCE: 13

Lys Leu Ala Lys Leu Ala Lys Lys Leu Ala Lys Leu Ala Lys
  1               5                  10

<210> SEQ ID NO 14
<211> LENGTH: 14
<212> TYPE: PRT
<213> ORGANISM: Artificial Sequence
```

```
<220> FEATURE:
<223> OTHER INFORMATION: synthetic construct

<400> SEQUENCE: 14

Lys Leu Ala Lys Lys Leu Ala Lys Leu Ala Lys Lys Leu Ala
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic construct

<400> SEQUENCE: 15

Lys Ala Ala Lys Lys Ala Ala Lys Ala Ala Lys Lys Ala Ala
1               5                   10

<210> SEQ ID NO 16
<211> LENGTH: 21
<212> TYPE: PRT
<213> ORGANISM: Artificial Sequence
<220> FEATURE:
<223> OTHER INFORMATION: synthetic construct

<400> SEQUENCE: 16

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 17
<211> LENGTH: 6
<212> TYPE: PRT
<213> ORGANISM: Artificial Sequence
<220> FEATURE:
<223> OTHER INFORMATION: synthetic construct

<400> SEQUENCE: 17

Cys Ser Arg Pro Arg Arg
1               5

<210> SEQ ID NO 18
<211> LENGTH: 13
<212> TYPE: PRT
<213> ORGANISM: Artificial Sequence
<220> FEATURE:
<223> OTHER INFORMATION: synthetic construct

<400> SEQUENCE: 18

Cys Tyr Ala Asp Cys Glu Gly Thr Cys Gly Met Val Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: synthetic construct

<400> SEQUENCE: 19

Cys Trp Asn Ile Cys Pro Gly Gly Cys Arg Ala Leu Cys
1               5                   10

<210> SEQ ID NO 20
<211> LENGTH: 12
<212> TYPE: PRT
```

```
<213> ORGANISM: Artificial Sequence
<220> FEATURE:
<223> OTHER INFORMATION: synthetic construct

<400> SEQUENCE: 20

Gly Pro Gly Cys Glu Glu Glu Cys Gln Pro Ala Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: synthetic construct

<400> SEQUENCE: 21

Cys Lys Gly Thr Cys Val Leu Gly Cys Ser Glu Glu Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: synthetic construct

<400> SEQUENCE: 22

Cys Ser Thr Leu Cys Gly Leu Arg Cys Met Gly Thr Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: synthetic construct

<400> SEQUENCE: 23

Cys Met Pro Arg Cys Gly Val Asn Cys Lys Trp Ala Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: synthetic construct

<400> SEQUENCE: 24

Cys Val Gly Ala Cys Asp Leu Lys Cys Thr Gly Gly Cys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: synthetic construct

<400> SEQUENCE: 25

Cys Val Ala Leu Cys Arg Glu Ala Cys Gly Glu Gly Cys
1               5                   10

<210> SEQ ID NO 26
<211> LENGTH: 13
<212> TYPE: PRT
<213> ORGANISM: Artificial Sequence
<220> FEATURE:
```

<223> OTHER INFORMATION: synthetic construct

<400> SEQUENCE: 26

Cys Ser Ser Gly Cys Ser Lys Asn Cys Leu Glu Met Cys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: synthetic construct

<400> SEQUENCE: 27

Cys Gly Arg Pro Cys Arg Gly Gly Cys Ala Ala Ser Cys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: synthetic construct

<400> SEQUENCE: 28

Cys Gln Gly Gly Cys Gly Val Ser Cys Pro Ile Phe Cys
1               5                   10

<210> SEQ ID NO 29
<211> LENGTH: 13
<212> TYPE: PRT
<213> ORGANISM: Artificial Sequence
<220> FEATURE:
<223> OTHER INFORMATION: synthetic construct

<400> SEQUENCE: 29

Cys Ala Val Arg Cys Asp Gly Ser Cys Val Pro Glu Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: synthetic construct

<400> SEQUENCE: 30

Cys Gly Phe Gly Cys Ser Gly Ser Cys Gln Met Gln Cys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: synthetic construct

<400> SEQUENCE: 31

Cys Arg Val Val Cys Ala Asp Gly Cys Arg Phe Ile Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic construct

```
<400> SEQUENCE: 32

Cys Thr Met Gly Cys Thr Ala Gly Cys Ala Phe Ala Cys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: synthetic construct

<400> SEQUENCE: 33

Cys Glu Gly Lys Cys Gly Leu Thr Cys Glu Cys Thr Cys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: synthetic construct

<400> SEQUENCE: 34

Cys Asn Gln Gly Cys Ser Gly Ser Cys Asp Val Met Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: synthetic construct

<400> SEQUENCE: 35

Cys Ala Ser Gly Cys Ser Glu Ser Cys Tyr Val Gly Cys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: synthetic construct

<400> SEQUENCE: 36

Cys Gly Gly Gly Cys Gln Trp Gly Cys Ala Gly Glu Cys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: synthetic construct

<400> SEQUENCE: 37

Cys Ser Val Arg Cys Lys Ser Val Cys Ile Gly Leu Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic construct

<400> SEQUENCE: 38
```

```
Cys Pro Ser Asn Cys Val Ala Leu Cys Thr Ser Gly Cys
 1               5                  10
```

<210> SEQ ID NO 39
<211> LENGTH: 13
<212> TYPE: PRT
<213> ORGANISM: Artificial Sequence
<220> FEATURE:
<223> OTHER INFORMATION: synthetic construct

<400> SEQUENCE: 39

```
Cys Val Glu Gly Cys Ser Ser Gly Cys Gly Pro Gly Cys
 1               5                  10
```

<210> SEQ ID NO 40
<211> LENGTH: 13
<212> TYPE: PRT
<213> ORGANISM: Artificial Sequence
<220> FEATURE:
<223> OTHER INFORMATION: synthetic construct

<400> SEQUENCE: 40

```
Cys Arg Val Val Cys Ala Asp Gly Cys Arg Leu Ile Cys
 1               5                  10
```

<210> SEQ ID NO 41
<211> LENGTH: 13
<212> TYPE: PRT
<213> ORGANISM: Artificial Sequence
<220> FEATURE:
<223> OTHER INFORMATION: synthetic construct

<400> SEQUENCE: 41

```
Cys Ser Thr Leu Cys Gly Leu Arg Cys Met Gly Thr Cys
 1               5                  10
```

<210> SEQ ID NO 42
<211> LENGTH: 13
<212> TYPE: PRT
<213> ORGANISM: Artificial Sequence
<220> FEATURE:
<223> OTHER INFORMATION: synthetic construct

<400> SEQUENCE: 42

```
Cys Phe Thr Phe Cys Glu Tyr His Cys Gln Leu Thr Cys
 1               5                  10
```